US012740973B2

(12) United States Patent
Geva et al.

(10) Patent No.: US 12,740,973 B2
(45) **Date of Patent: *Sep. 22, 2026**

(54) TREATMENT OF NEURODEGENERATIVE EYE DISEASE USING PRIDOPIDINE

(71) Applicant: PRILENIA NEUROTHERAPEUTICS LTD., Herzliya (IL)

(72) Inventors: Michal Geva, Even-Yehuda (IL); Hermann Kurt Russ, Altendorf (CH); Ralph Laufer, Tel Aviv (IL); Aric Orbach, Rehovot (IL)

(73) Assignee: Prilenia Neurotherapeutics Ltd., Yakum (IL)

( * ) Notice: Subject to any disclaimer, the term of this patent is extended or adjusted under 35 U.S.C. 154(b) by 1294 days.

This patent is subject to a terminal disclaimer.

(21) Appl. No.: 17/513,239

(22) Filed: Oct. 28, 2021

(65) Prior Publication Data

US 2022/0062255 A1 Mar. 3, 2022

Related U.S. Application Data

(63) Continuation-in-part of application No. 17/498,075, filed on Oct. 11, 2021, now abandoned, and a continuation-in-part of application No. 16/078,929, filed as application No. PCT/US2017/019266 on Feb. 24, 2017, now Pat. No. 11,738,012.

(60) Provisional application No. 62/299,290, filed on Feb. 24, 2016.

(51) Int. Cl.

| | |
|---|---|
| ***A61K 31/451*** | (2006.01) |
| ***A61K 9/00*** | (2006.01) |
| ***A61P 27/06*** | (2006.01) |

(52) U.S. Cl.

CPC .......... *A61K 31/451* (2013.01); *A61K 9/0048* (2013.01); *A61P 27/06* (2018.01)

(58) Field of Classification Search

CPC ................ A61K 31/451; A61K 9/0048; A61P 27/02–14

See application file for complete search history.

(56) References Cited

U.S. PATENT DOCUMENTS

| | | | | |
|---|---|---|---|---|
| 6,903,120 | B2 | 6/2005 | Sonesson et al. | |
| 7,417,043 | B2 | 8/2008 | Sonesson et al. | |
| 7,579,474 | B2 | 8/2009 | Sonesson et al. | |
| 7,923,459 | B2 | 4/2011 | Gauthier et al. | |
| 9,006,445 | B2 | 4/2015 | Sonesson et al. | |
| 9,012,476 | B2 | 4/2015 | Zimmermann et al. | |
| 9,139,525 | B2 | 9/2015 | Wikström | |
| 9,340,555 | B2 | 5/2016 | Guo et al. | |
| RE46,117 | E | 8/2016 | Sonesson et al. | |
| 9,796,673 | B2 | 10/2017 | Wu et al. | |
| 9,814,706 | B2 | 11/2017 | Zimmermann et al. | |
| 10,047,049 | B2 | 8/2018 | Barel et al. | |
| 10,130,621 | B2 | 11/2018 | Schmidt et al. | |
| 10,322,119 | B2 | 6/2019 | Bassan et al. | |
| 10,406,145 | B2 | 9/2019 | Schmidt et al. | |
| 10,603,311 | B2 | 3/2020 | Geva et al. | |
| 11,738,012 | B2 * | 8/2023 | Russ .................. | A61K 31/451 514/226.5 |
| 2003/0139423 | A1 | 7/2003 | Sonesson et al. | |
| 2007/0238878 | A1 | 10/2007 | Desmond et al. | |
| 2009/0062400 | A1 | 3/2009 | Oron et al. | |
| 2010/0197712 | A1 | 8/2010 | Carlsson et al. | |
| 2010/0316731 | A1 | 12/2010 | Weinstock et al. | |
| 2011/0206782 | A1 | 8/2011 | Zhang | |
| 2013/0150406 | A1 | 6/2013 | Zimmermann et al. | |
| 2013/0197031 | A1 | 8/2013 | Sonesson | |
| 2013/0267552 | A1 | 10/2013 | Waters et al. | |
| 2014/0088140 | A1 | 3/2014 | Hayden et al. | |
| 2014/0088144 | A1 | 3/2014 | Egan | |
| 2014/0088145 | A1 | 3/2014 | Hayden et al. | |
| 2015/0202302 | A1 | 7/2015 | Licht et al. | |
| 2016/0095847 | A1 | 4/2016 | Sonesson | |
| 2016/0166559 | A1 | 6/2016 | Sonesson | |
| 2016/0243098 | A1 | 8/2016 | Geva et al. | |
| 2017/0020854 | A1 | 1/2017 | Licht et al. | |
| 2017/0266170 | A1 | 9/2017 | Waters et al. | |
| 2018/0055832 | A1 | 3/2018 | Hayden et al. | |
| 2018/0235950 | A1 | 8/2018 | Sonesson et al. | |
| 2019/0015401 | A1 | 1/2019 | Sonesson | |
| 2019/0209542 | A1 | 7/2019 | Licht et al. | |
| 2019/0350915 | A1 | 11/2019 | Bassan et al. | |

(Continued)

FOREIGN PATENT DOCUMENTS

| | | |
|---|---|---|
| WO | WO 2001/046144 | 6/2001 |
| WO | WO 2001/046145 | 6/2001 |

(Continued)

OTHER PUBLICATIONS

Hosoya et al. "Roles of the conjunctiva in ocular drug delivery: a review of conjunctival transport mechanisms and their regulation," Eur. J. Pharm. Biopharm. 2005;60(2):227-40. PMID: 15939235. (Year: 2005).*

Ha et al., "Late-onset inner retinal dysfunction in mice lacking sigma receptor 1 (σR1)," Invest. Ophthalmol. Vis. Sci. 2011;52(10):7749-60. PMID: 21862648. (Year: 2011).*

Sahlholm et al., "Pridopidine selectively occupies sigma-1 rather than dopamine D2 receptors at behaviorally active doses," Psychopharmacology (Berl). Sep. 2015;232(18):3443-53. PMID: 26159455. (Year: 2015).*

Ahmad, Saeed. Letters to the Editor: Fluoxetine and glaucoma. Annals of Pharmacotherapy, 1991, vol. 25, 436.

Almasieh et al. "A cell-permeable phosphine-borane complex delays retinal ganglion cell death after axonal injury through activation of the pro-survival extracellular signal-regulated kinases 1/2 pathway" Journal of neurochemistry. Sep. 2011;118(6):1075-86.

(Continued)

*Primary Examiner* — Theodore R. Howell

(74) *Attorney, Agent, or Firm* — Mark S. Cohen; PEARL COHEN LLP

(57) ABSTRACT

This application provides a method of treating a subject afflicted with a neurodegenerative eye disease comprising administering to the subject an amount of pridopidine effective to treat the subject, pharmaceutical composition and uses and applications thereof.

11 Claims, 12 Drawing Sheets

(56) References Cited

U.S. PATENT DOCUMENTS

| | | | |
|---|---|---|---|
| 2020/0000785 | A1 | 1/2020 | Waters et al. |
| 2020/0030308 | A1 | 1/2020 | Schmidt et al. |
| 2020/0092813 | A1 | 3/2020 | Kim et al. |

FOREIGN PATENT DOCUMENTS

| | | | |
|---|---|---|---|
| WO | WO/2004/103263 | | 12/2004 |
| WO | WO 2005/073233 | A1 | 8/2005 |
| WO | 2005/121092 | A1 | 12/2005 |
| WO | WO 2006/029253 | A2 | 3/2006 |
| WO | WO 2006/040155 | | 4/2006 |
| WO | WO 2006/073519 | A1 | 7/2006 |
| WO | WO 2007/042295 | A1 | 4/2007 |
| WO | WO 2008/127188 | | 10/2008 |
| WO | 2008/155357 | A2 | 12/2008 |
| WO | 2011/107583 | A1 | 9/2011 |
| WO | WO 2012/028635 | | 3/2012 |
| WO | WO 2013/034622 | | 3/2013 |
| WO | WO 2013/086425 | | 6/2013 |
| WO | WO 2013/152105 | | 10/2013 |
| WO | WO 2014/205229 | | 12/2014 |
| WO | WO 2015/112601 | | 7/2015 |
| WO | WO 2016/003919 | | 1/2016 |
| WO | WO 2016/138130 | | 9/2016 |
| WO | WO 2016/138135 | | 9/2016 |
| WO | WO 2017/015609 | | 1/2017 |
| WO | WO 2017/015615 | | 1/2017 |
| WO | WO 2017/189958 | A1 | 11/2017 |

OTHER PUBLICATIONS

Almasieh et al. “Axonal degeneration in retinal ganglion cells is associated with a membrane polarity-sensitive redox process” Journal of Neuroscience. Apr. 5, 2017;37(14):3824-39.

Alward WL. “Medical management of glaucoma” New England Journal of Medicine. Oct. 29, 1998;339(18):1298-307.

“A Phase 2, to Evaluating the Safety and Efficacy of Pridopidine Vs Placebo for Symptomatic Treatment in Patients With Huntington’s Disease” 2013; downloaded from Internet: https://www.clinicaltrials.gov/ct2/show/NCT02006472.

Bermack et al. (2005)—Distinct modulatory roles of sigma receptor subtypes on glutamatergic responses in the dorsal hippocampus—Synapse, 55(1), 37-44.

Booth et al. “Redox nanodomains are Induced by and control calcium signaling at the ER-mitochondrial interface” Molecular cell. Jul. 21, 2016;63(2):240-8.

Cantarella et al. (2007)—Protective effects of the sigma agonist Pre-084 in the rat retina—British journal of ophthalmology, 91(10), 1382-1384.

Catrinescu et al. “Superoxide signaling and cell death in retinal ganglion cell axotomy: Effects of metallocorroles” Experimental eye research. Apr. 1, 2012;97(1):31-5.

Chou et al. (1999)—Binding of dimemorfan to sigma-1 receptor and its anticonvulsant and locomotor effects in mice, compared with dextromethorphan and dextrorphan—Brain research, 821(2), 516-519.

Chrysostomou et al. “Oxidative stress and mitochondrial dysfunction in glaucoma” Current opinion in pharmacology. Feb. 1, 2013;13(1):12-5.

Coleman “Glaucoma” Lancet Nov. 20, 1999;354(9192):1803-10.

Cone et al. “The effects of anesthesia, mouse strain and age on intraocular pressure and an improved murine model of experimental glaucoma” Experimental eye research. Jun. 1, 2012:99:27-35.

CSID:25948790, www.chemspider.com/Chemical-Structure.25948790.html (accessed 23:27, Jul. 15, 2016).

CSID:7971505, www.chemspider.com/Chemical-Structure.7971505.html (accessed 23:33, Jul. 15, 2016).

De Yebenes et al. (2011)—Pridopidine for the treatment of motor function in patients with Huntington’s disease (MermaiHD): a phase 3, randomized, double-blind, placebo-controlled trial—The Lancet Neurolog, vol. 10, not 12, p. 1049-1057.

Dun et al. “Prevention of excitotoxicity in primary retinal ganglion cells by (+)-pentazocine, a sigma receptor-1-specific ligand” Investigative ophthalmology & visual science. Oct. 1, 2007;48(10):4785-94.

Dyhring et al. The dopaminergic stabilizers pridopidine (ACR16) and (−)-OSU6162 display dopamine D2 receptor antagonism and fast receptor dissociation properties. European journal of pharmacology, 2010, 628.1-3: 19-26.

Eddings et al. “Pridopidine protects neurons from mutant-huntingtin toxicity via the sigma-1 receptor” Neurobiology of disease. Sep. 1, 2019;129:118-29.

Ellis et al. “Sigma-1 receptor regulates mitochondrial function in glucose-and oxygen-deprived retinal ganglion cells” ony Investigative ophthalmology & visual science. May 1, 2017;58(5):2755-64.

Ergorul et al. “Solving the lost in translation problem: improving the effectiveness of translational research” Current opinion in pharmacology. Feb. 1, 2013;13(1):108-14.

Farkas et al. “Apoptosis, neuroprotection, and retinal ganglion cell death: an overview” International ophthalmology clinics. Jan. 1, 2001;41(1):111-30.

Ferreira et al. “Co-agonists differentially tune GluN2B-NMDA receptor trafficking at hippocampal synapses” Elife. Jun. 9, 2017;6:e25492.

Francardo et al. (2014)—Pharmacological stimulation of sigma-1 receptors has neurorestorative effects in experimental parkinsonism—Brain, 137(7), 1998-2014.

Francardo et al. “Pridopidine induces functional neurorestoration via the sigma-1 receptor in a mouse model of Parkinson’s disease” Neurotherapeutics. Apr. 2019;16(2):465-79.

Geva et al. (2016)—Pridopidine activates neuroprotective pathways impaired in Huntington Disease—Human molecular genetics, 25(18), 3975-3987.

Ghaffarieh et al. “Optic nerve disease and axon pathophysiology” International review of neurobiology. Jan. 1, 2012;105:1-7.

Gueven et al. “Targeting mitochondrial function to treat optic neuropathy” Mitochondrion. Sep. 1, 2017;36:7-14.

Gundlach et al. (1986)—Autoradiographic localization of sigma receptor binding sites in guinea pig and rat central nervous system with (+) 3H-3-(3-hydroxyphenyl)-N-(1-propyl) piperidine—Journal of Neuroscience, 6(6), 1757-1770.

Gupta et al. (2016)—Glaucoma—American Family Physician 93(8):668-674.

Gupta et al. “Protective effects of 7, 8-dihydroxyflavone on retinal ganglion and RGC-5 cells against excitotoxic and oxidative stress” Journal of Molecular Neuroscience. Jan. 2013;49(1):96-104.

Ha et al. “Late-onset inner retinal dysfunction in mice lacking sigma receptor 1 (σR1)” Investigative ophthalmology & visual science. Sep. 1, 2011;52(10):7749-60.

Hayashi et al. (2005)—The sigma receptor: evolution of the concept in neuropsychopharmacology—Current neuropharmacology, 3(4), 267-280.

Hayashi et al. (2001)—Regulating ankyrin dynamics: Roles of sigma-1 receptors—Proceedings of the National Academy of Sciences, 98(2), 491-496.

Hayashi et al. “Sigma-1 receptor chaperones at the ER-mitochondrion interface regulate Ca2+ signaling and cell survival” Cell. Nov. 2, 2007;131(3):596-610.

Hiramatsu et al. Improvement of memory impairment by (+)-and (−)-pentazocine via sigma, but not kappa opioid receptors. Brain research, 2005, 1057.1-2: 72-80.

Hong et al. (2004)—Modulation of bradykinin-induced calcium changes in SH—SY5Y cells by neurosteroids and sigma receptor ligands via a shared mechanism—Synapse, 54(2), 102-110.

Huntington Study Group Hart Investigators (2013)—A randomized, double-blind, placebo-controlled trial of pridopidine in Huntington’s disease—Movement Disorders, vol. 28, not 10, pp. 1407-1415. First published Feb. 28, 2013.

Hyrskyluoto et al. (2013)—Sigma-1 receptor agonist PRE084 is protective against mutant huntingtin-induced cell degeneration: involvement of calpastatin and the NF-κ B pathway—Cell death & disease, 4(5), e646-e646.

(56) References Cited

OTHER PUBLICATIONS

International Search Report for PCT Application No. PCT/US2017/019266 dated May 10, 2017.
Ionescu et al. "Targeting the sigma-1 receptor via pridopidine ameliorates central features of ALS pathology in a SOD1 G93A model" Cell death & disease. Mar. 2019 1;10(3):1-9.
Jiménez-Jiménez et al. Aggravation of glaucoma with fluvoxamine. *Annals of Pharmacotherapy*, 2001, 35.12: 1565-1566.
Johnston et al. Pridopidine, a clinic-ready compound, reduces 3, 4-dihydroxyphenylalanine-induced dyskinesia in Parkinsonian macaques. *Movement Disorders*, 2019, 34.5: 708-716.
Kalesnykas et al. "The expression of heat shock protein 27 in retinal ganglion and glial cells in a rat glaucoma model" Neuroscience. Dec. 12, 2007;150(3):692-704.
Kamei J. "Possible role of sigma-receptors in the regulation of cough reflex, gastrointestinal and retinal function. Nihon yakurigaku zasshi" Folla pharmacologica Japonica. Jul. 1, 1999;114(1):35-41.
Kanamori et al. "Neuroprotection against superoxide anion radical by metallocorroles in cellular and murine models of optic neuropathy" Journal of neurochemistry. Jul. 2010;114(2):488-98.
Kanamori et al. "In vivo imaging of retinal ganglion cell axons within the nerve fiber layer" Investigative ophthalmology & visual science. Apr. 1, 2010;51(4):2011-8.
Kimura et al. "Neuroprotection, growth factors and BDNF-TrkB signalling in retinal degeneration" International journal of molecular sciences. Sep. 2016;17(9):1584.
Kipnis et al. "T cell immunity to copolymer 1 confers neuroprotection on the damaged optic nerve: possible therapy for optic neuropathies" Proceedings of the National Academy of Sciences. Jun. 20, 2000;97(13):7446-51.
Kuehn et al. "Retinal ganglion cell death in glaucoma: mechanisms and neuroprotective strategies" development. 2005;1:32005.
Kusko et al. "Large-scale transcriptomic analysis reveals that pridopidine reverses aberrant gene expression and activates neuroprotective pathways in the YAC128 HD mouse" Molecular neurodegeneration. Dec. 2018;13(1):1-5.
Levin et al. "Lost in translation: bumps in the road between bench and bedside" Jama. Apr. 21, 2010;303(15):1533-4.
Levin et al. "History of neuroprotection and rationale as a therapy for glaucoma" Am J Manag Care. Feb. 1, 2008;14(1 Suppl):S11-14.
Levin et al. "The academic-industrial complexity: failure to launch" Trends in pharmacological sciences. Dec. 1, 2017;38(12):1052-60.
Lima et al. Serotonin Inhibits outgrowth of goldfish retina and impairs the trophic effect of taurine. *Journal of neuroscience research*, 1994, 38.4: 444-450.
Lucas et al. (2008)—Further evidence for an antidepressant potential of the selective σ1 agonist SA 4503: electrophysiological, morphological and behavioural studies—International Journal of Neuropsychopharmacology, 11(4), 485-495.
Luedtke et al. (2012)—high affinity sigma 1 receptor selective compounds—Brain research, 1441, 17-26.
Lysen et al. "Idebenone: a review in Leber's hereditary optic neuropathy" Drugs. May 1, 2016;76(7):805-13.
Lyseng-Williamson KA. "Idebenone: a review in Leber's hereditary optic neuropathy" Drugs. May 1, 2016;76(7):805-13.
Matsuno et al. (1992)—Increase of extracellular acetylcholine level in rat frontal cortex induced by (+) N-allylnormetazocine as measured by brain microdialysis—Brain Research, 575(2), 315-319.
Matsuno et al.(1993)—Similar ameliorating effects of benzomorphans and 5-HT 2 antagonists on drug-induced impairment of passive avoidance response in mice: comparison with acetylcholinesterase inhibitors—Psychopharmacology, 112(1), 134-141.
Matsuno et al.(1994)—Ameliorating effects of σ receptor ligands on the impairment of passive avoidance tasks in mice: involvement in the central acetylcholinergic system—European journal of pharmacology, 261(1-2), 43-51.
Maurice et al. (2001)—The interaction between neuroactive steroids and the σ1 receptor function: behavioral consequences and therapeutic opportunities—Brain Research Reviews, 37(1-3), 116-132.
Maurice et al.(1994)—Behavioral evidence for a modulating role of σ ligands in memory processes. I. Attenuation of dizocilpine (MK-801)-induced amnesia—Brain research, 647(1), 44-56.
Maurice, T.(1997)—Neuroprotective and anti-amnesic potentials of sigma (σ) receptor ligands—Progress in Neuro-Psychopharmacology and Biological Psychiatry, 21(1), 69-102.
Mavlyutov et al. "Subcellular localization of the sigma-1 receptor in retinal neurons—an electron microscopy study" Scientific reports. Jun. 2, 2015;5(1):1-11.
Mavlyutov et al. "Accelerated retinal ganglion cell death in mice deficient in the Sigma-1 receptor" Molecular vision. 2011;17:1034.
Mirzaei et al. "Age-related neurodegenerative disease associated pathways identified in retinal and vitreous proteome from human glaucoma eyes" Scientific reports. Oct. 4, 2017;7(1):1-6.
Monnet, F. P. (2005)—Sigma-1 receptor as regulator of neuronal intracellular Ca2+: clinical and therapeutic relevance—Biology of the Cell, 97(12), 873-883.
Monnet et al. (1992)—Neuropeptide Y potentiates the N-methyl-D-aspartate response in the CA3 dorsal hippocampus. II. Involvement of a subtype of sigma receptor—Journal of Pharmacology and Experimental Therapeutics, 263(3), 1219-1225.
Monnet et al.(1990)-N-methyl-D-aspartate-induced neuronal activation is selectively modulated by σ receptors—European journal of pharmacology, 179(3), 441-445.
Monnet et al.(1992)—Modulation by sigma ligands of N-methyl-D-aspartate-induced [3 H] noradrenaline release in the rat hippocampus: G-protein dependency-Naunyn-Schmiedeberg's archives of pharmacology, 346(1), 32-39.
Monnet et al.(2006)—The σ1 protein as a target for the non-genomic effects of neuro (active) steroids: molecular, physiological, and behavioral aspects. Journal of pharmacological sciences, 100, 93-118.
Mueller et al. "Sigma-1 receptor stimulation protects retinal ganglion cells from ischemia-like insult through the activation of extracellular-signal-regulated kinases ½" Experimental eye research. Nov. 1, 2014;128:156-69.
Mueller BH. "Neuroprotective properties of sigma-1 receptor in glaucoma" University of North Texas Health Science Center at Fort Worth; 2014.
Munemasa et al. "Modulation of mitochondria in the axon and soma of retinal ganglion cells in a rat glaucoma model" Journal of neurochemistry. Dec. 2010;115(6):1508-19.
Mysona et al. "Role of BDNF/TrkB pathway in the visual system: therapeutic implications for glaucoma" Expert review of ophthalmology. Jan. 2, 2017;12(1):69-81.
Mysona et al. "Relationship between Sigma-1 receptor and BDNF in the visual system" Experimental eye research. Feb. 1, 2018;167:25-30.
Mysona et al. "The role of sigma 1 receptor as a neuroprotective target in glaucoma" Sigma Receptors: Their Role in Disease and as Therapeutic Targets. 2017:299-307.
Naia et al. "Comparative mitochondrial-based protective effects of resveratrol and nicotinamide in Huntington's disease models" Molecular neurobiology. Sep. 2017;54(7):5385-99.
Niemuth et al. "Intracellular disulfide reduction by phosphine-borane complexes: Mechanism of action for neuroprotection" Neurochemistry international. Oct. 1, 2016;99:24-32.
Nita et al. "The role of the reactive oxygen species and oxidative stress in the pathomechanism of the age-related ocular diseases and other pathologies of the anterior and posterior eye segments in adults" Oxidative medicine and cellular longevity. Oct. 2016;2016.
Okoye et al. "Increased expression of brain-derived neurotrophic factor preserves retinal function and slows cell death from rhodopsin mutation or oxidative damage" Journal of Neuroscience. May 15, 2003;23(10):4164-72.
Ola et al. (2001)—Expression pattern of sigma receptor 1 mRNA and protein in mammalian retina—Molecular brain research, 95(1-2), 86-95.
Onyango et al. "Mitochondrial dysfunction in Alzheimer's disease and the rationale for bioenergetics based therapies" Aging and disease. Mar. 2016;7(2):201.

(56) References Cited

OTHER PUBLICATIONS

Owens et al. "Neurotransmitter receptor and transporter binding profile of antidepressants and their metabolites" Journal of Pharmacology and Experimental Therapeutics. Dec. 1, 1997;283(3):1305-22.

Pal et al. "The sigma-1 receptor protects against cellular oxidative stress and activates antioxidant response elements" European journal of pharmacology. May 5, 2012;682(1-3):12-20.

Pande et al. (1999). A placebo-controlled trial of igmesine in the treatment of major depression. *European Neuropsychopharmacology*, (9), 138.

Ponten et al (2010). In vivo pharmacology of the dopaminergic stabilizer pridopidine. European journal of pharmacology, 644(1-3), 88-95.

Ponten et al. "The dopaminergic stabilizer pridopidine decreases expression of L-DOP-induced locomotor sensitisation in the rat unilateral 6-OHDA model" European journal of pharmacology. Jan. 5, 2013;698(1-3):278-85.

Rabinovich-Guilatt et al. (2016)—The effect of mild and moderate renal impairment on the pharmacokinetics of pridopidine, a new drug for Huntington's disease—British journal of clinical pharmacology, 81(2), 246-255.

Ragauskas et al. "Early retinal function deficit without prominent morphological changes in the R6/2 mouse model of Huntington's disease" PLoS One. Dec. 3, 2014;9(12):e113317.

Rousseaux et al. (2016). Sigma receptors [≐ Rs]: biology in normal and diseased states. Journal of Receptors and Signal Transduction, 36(4), 327-388.

Ryskamp et al. The sigma-1 receptor mediates the beneficial effects of pridopidine in a mouse model of Huntington disease. Neurobiology of disease, 2017, 97: 46-59.

Ryskamp et al. "Neuronal sigma-1 receptors: signaling functions and protective roles in neurodegenerative diseases" impair Frontiers in neuroscience. Aug. 28, 2019;13:862.

Ryskamp et al. "Pridopidine stabilizes mushroom spines in mouse models of Alzheimer's disease by acting on the sigma-1 receptors" Neurobiology of disease. Apr. 1, 2019;124:489-504.

Sahlholm et al. "Pridopidine selectively occupies sigma-1 rather than dopamine D2 receptors at behaviorally active doses" Psychopharmacology. Sep. 2015;232(18):3443-53.

Sahlholm et al. "The dopamine stabilizers ACR16 and (−)-OSU6162 display nanomolar affinities at the σ-1 receptor" Molecular psychiatry. Jan. 2013;18(1):12-4.

Sanchez et al. "Emerging mitochondrial therapeutic targets in optic neuropathies" Pharmacology & therapeutics. Sep. 1, 2016;165:132-52.

Schwartz et al. "'Axogenic' and 'somagenic' neurodegenerative diseases: definitions and therapeutic implications" Molecular medicine today. Nov. 1, 1999;5(11):470-3.

Sheng et al. "Mitochondrial transport in neurons: impact on synaptic homeostasis and neurodegeneration" Nature Reviews Neuroscience. Feb. 2012;13(2):77-93.

Shimazawa et al. "Effect of a sigma-1 receptor agonist, cutamesine dihydrochloride (SA4503), on photoreceptor cell death against light-induced damage" Experimental eye research. Mar. 1, 2015;132:64-72.

Skrzycki et al. "Multiple protective functions of sigmat receptor" Current Protein and Peptide Science. Dec. 1, 2014;15(8):798-811.

Smith et al. (2008)—In vivo protection against retinal neurodegeneration by sigma receptor 1 ligand (+)-pentazocine—Investigative ophthalmology & visual science, 49(9), 4154-4161.

Smith-Dijak et al. "Impairment and restoration of homeostatic plasticity in cultured cortical neurons from a mouse model of huntington disease" Frontiers in cellular neuroscience. May 16, 2019;13:209.

Squitieri et al. "Profile of pridopidine and its potential in the treatment of Huntington disease: the evidence to date" Drug design, development and therapy. 2015;9:5827.

Squitieri et al. "Pridopidine, a dopamine stabilizer, improves motor performance and shows neuroprotective effects in Huntington disease R6/2 mouse model" Journal of cellular and molecular medicine. Nov. 2015;19(11):2540-8.

Sun et al. Pregnenolone sulfate decreases intraocular pressure and changes expression of sigma receptor in a model of chronic ocular hypertension. Molecular biology reports, 2012, 39.6: 6607-6614.

Supplementary European Search Report for European Application No. 17757261.7 dated Jun. 6, 2019.

Tchedre et al. "σ-1 receptors protect RGC-5 cells from apoptosis by regulating intracellular calcium, Bax levels, and caspase-3 activation" Investigative ophthalmology & visual science. Jun. 1, 2008;49(6):2577-88.

Urani et al. (2004)—Enhanced antidepressant efficacy of σ1 receptor agonists in rats after chronic intracerebroventricular infusion of β-amyloid-(1-40) protein—European journal of pharmacology, 486(2), 151-161.

Vagnerova et al. "Sigma 1 receptor agonists act as neuroprotective drugs through inhibition of inducible nitric oxide synthase" Anesthesia & Analgesia. Aug. 1, 2006;103(2):430-4.

Van Niel et al. Efficacy of full μ-opioid receptor agonists is not impaired by concomitant buprenorphine or mixed opioid agonists/antagonists—preclinical and clinical evidence. *Drug research*, 2016, 66.11: 562-570.

Vecino et al. "Rat retinal ganglion cells co-express brain derived neurotrophic factor (BDNF) and its receptor TrkB" Vision research. Jan. 1, 2002;42(2):151-7.

Volz et al.(2004)—Clinical trials with sigma ligands—Pharmacopsychiatry, 37(S 3), 214-220.

Wang et al.(2016)—Activation of the molecular chaperone, sigma 1 receptor, preserves cone function in a murine model of inherited retinal degeneration—Proceedings of the National Academy of Sciences, 113(26), E3764-E3772.

Wang et al. (2016)—Role of Sigma 1 Receptor in retinal degeneration of the Ins2Akita/+ murine model of diabetic retinopathy—Investigative Ophthalmology & Visual Science, 57(6), 2770-2781.

Wang et al. Comparison of Sigma 1 Receptor Ligands SA4503 and PRE084 to (+)-Pentazocine in the rd10 Mouse Model of RP. *Investigative ophthalmology & visual science*, 2020, 61.13: 3-3.

Wang et al. "Absence of sigma 1 receptor accelerates photoreceptor cell death in a murine model of retinitis pigmentosa" Investigative ophthalmology & visual science. Sep. 1, 2017;58(11):4545-58.

Weinreb et al. "Is neuroprotection a viable therapy for glaucoma?" Archives of ophthalmology. Nov. 1, 1999;117(11):1540-4.

Weng et al. "Loss of sigma-1 receptor chaperone promotes astrocytosis and enhances the Nrf2 antioxidant defense" Oxidative medicine and cellular longevity. Oct. 2017;2017.

Zelefsky et al. Escitalopram-induced uveal effusions and bilateral angle closure glaucoma. *American journal of ophthalmology*, 2006, 141.6: 1144-1147.

Francardo, V., et al. (2019). Pridopidine induces functional neurorestoration via the sigma-1 receptor in a mouse model of Parkinson's disease. Neurotherapeutics, 16(2), 465-479.

Hellewell, S. B., et al. (1994). Rat liver and kidney contain high densities of σ1 and σ2 receptors: characterization by ligand binding and photoaffinity labeling. European Journal of Pharmacology: Molecular Pharmacology, 268(1), 9-18.

Jiménez-Jiménez, F. J., et al. (2001). Aggravation of glaucoma with fluvoxamine. Annals of Pharmacotherapy, 35(12), 1565-1566.

Rousseaux, C. G., & Greene, S. F. (2016). Sigma receptors [σ Rs]: biology in normal and diseased states. Journal of Receptors and Signal Transduction, 36(4), 327-388.

Shu, H., et al. (2011). Pentazocine-induced antinociception is mediated mainly by μ-opioid receptors and compromised by κ-opioid receptors in mice. The Journal of pharmacology and experimental therapeutics, 338(2), 579-587.

Smith-Dijak, A. I., et al. (2019). Impairment and restoration of homeostatic plasticity in cultured cortical neurons from a mouse model of Huntington disease. Frontiers in cellular neuroscience, 13, 209.

(56) References Cited

OTHER PUBLICATIONS

Zelefsky, J. R., et al. (2006). Escitalopram-induced uveal effusions and bilateral angle closure glaucoma. American journal of ophthalmology, 141(6), 1144-1147.

* cited by examiner

Intraocular Pressure

IOP (mmHg)

37
35
33
31
29
27
25
23
21
19
17

0
14
21
28
35
41

Day of Study

OD DDW
OD 3 mg/kg
OD 30 mg/kg
OD 60 mg/kg
OS DDW
OS 3 mg/kg
OS 30 mg/kg
OS 60 mg/kg

TREATMENT OF NEURODEGENERATIVE EYE DISEASE USING PRIDOPIDINE

CROSS-REFERENCE TO RELATED APPLICATIONS

This Application is a Continuation in Part Application from U.S. application Ser. No. 16/078,929 filed on Aug. 22, 2018; which is a National Phase Application of PCT International Application No. PCT/US2017/019266, International Filing Date Feb. 24, 2017; which claims the benefit of U.S. Provisional Application No. 62/299,290, filed Feb. 24, 2016; this Application is also a Continuation in Part Application from United-States application Ser. No. 17/498,075 filed Oct. 11, 2021; the entire contents of which are hereby incorporated by reference herein.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

FIELD OF THE INVENTION

This application provides a method of treating a subject afflicted with a neurodegenerative eye disease comprising systemically or topically administering to the subject an amount of pridopidine effective to treat the subject, pharmaceutical composition and uses and applications thereof.

BACKGROUND

Glaucoma is a group of ocular diseases characterized by progressive damage to the eye at least partly due to elevated intraocular pressure (IOP) (Merck Manual of Diagnosis and Therapy (1999)). Additionally, glaucoma is characterized by retinal ganglion cell (RGC) death, axon loss and an excavated appearance of the optic nerve head (Alward 1998). The classification of glaucoma includes several subtypes including for example, primary angle-closure glaucoma, secondary open-angle glaucoma, steroid-induced glaucoma, traumatic glaucoma, pigmentary dispersion syndrome, pseudoexfoliation syndrome, secondary angle-closure glaucoma, neovascular glaucoma, uveitis, and glaucoma and other eye pathologies. Other neurodegenerative diseases of the eye include different forms of macular degeneration, retinitis pigmentosa and all types of optic neuropathy.

Glaucoma can be diagnosed before vision loss occurs by visual field testing and by ophthalmoscopic examination of the optic nerve to detect "cupping." The mean IOP in normal adults is 15 to 16 mm Hg; the normal range is 10 to 21 mm Hg. One form of management of glaucoma is based on lowering the IOP using topically applied medications (Coleman 1999).

However, despite the availability of treatments for lowering IOP, many patients will continue to lose their vision due to RGC death and degeneration of the optic nerve (Mysona et al. 2017). As a result, therapies aimed at the preservation of RGCs, their axons and dendrites are the focus of many years of research.

Glaucomatous optic neuropathy appears to result from specific pathophysiological changes and subsequent death of RGCs and their axons. The process of RGC death is thought to be biphasic: a primary injury responsible for initiation of damage followed by a slower, secondary degeneration attributable to the hostile environment surrounding the degenerating cells (Kipnis et al. 2000).

The molecular mechanism triggering RGC death has not been identified. Deprivation of neurotrophic factors, ischemia, chronic elevation of glutamate or amyloid beta oligomers and impaired nitric oxide metabolism are suspected to be possible mechanisms (Farkas et al. 2001). In addition, it is possible that the mechanisms leading to RGC death share common features with other types of neuronal injury, such as elevated reactive oxygen species, disrupted $Ca^{2+}$ homeostasis, ER stress or induction of transcriptionally regulated cell death (Weinreb et al. 1999).

Pridopidine

Pridopidine (formerly ACR16,Huntexil®) is a highly potent and highly selective sigma-1 receptor (S1R) agonist in clinical development for neurodegenerative diseases including Huntington disease (HD) and amyotrophic lateral sclerosis (ALS). The chemical name of pridopidine is 4-(3-(Methylsulfonyl)phenyl)-1-propylpiperidine, and its Chemical Registry Number is CAS 346688-38-8 (CSID:7971505, 2016). The Chemical Registry number of pridopidine hydrochloride is 882737-42-0 (CSID:25948790 2016). Processes of synthesis of pridopidine and a pharmaceutically acceptable salt thereof are disclosed in U.S. Pat. No. 7,923,459 and PCT Application Publication No. WO 2017/015609. U.S. Pat. No. 6,903,120 claims pridopidine for the treatment of Parkinson's disease, dyskinesias, dystonias, Tourette's disease, iatrogenic and non-iatrogenic psychoses and hallucinoses, mood and anxiety disorders, sleep disorder, autism spectrum disorder, ADHD, Huntington's disease, age-related cognitive impairment, and disorders related to alcohol abuse and narcotic substance abuse.

The neuroprotective effects of pridopidine via S1R activation have been demonstrated in several in vitro and in vivo models of neurodegenerative diseases including HD, Alzheimer's disease (AD), Amyotrophic Lateral Sclerosis (ALS) and Parkinson's disease (PD) (Eddings et al. 2019; Ryskamp et al. 2019; Ionescu et al. 2019; Francardo et al. 2019).

The effects of pridopidine on neurodegenerative eye diseases, in particular glaucoma, have not been reported previously.

SUMMARY OF THE INVENTION

The subject invention provides a method of treating, reducing or inhibiting a symptom of neurodegenerative eye disease in a subject afflicted with a neurodegenerative eye disease comprising administering to the subject a composition comprising pridopidine or pharmaceutically acceptable salt thereof.

In other embodiments the symptom is an optic nerve axon damage or loss. In other embodiments, the symptom is a retinal ganglion cell (RGC) loss or death. In other embodiments, the composition is effective to reduce or prevent optic nerve axon loss or damage in a subject. In other embodiments, the composition is effective to reduce or prevent a retinal ganglion cell (RGC) loss or death in a subject.

In other embodiments, the optic nerve axon loss is reduced by at least 3%, by at least 5%, by at least 10%, by at least 20%, by at least 30%, by at least 40% or by at least 50%. In other embodiments, the optic nerve axon loss is reduced by more than 50%, more than 60%, more than 70%, or more than 80%. In other embodiments, the composition is effective to protect an optic nerve axon from degeneration in the subject. In other embodiments, the axon degeneration is induced by elevated intraocular pressure.

The subject invention provides a method of treating a subject afflicted with a neurodegenerative eye disease comprising administering to the subject a pharmaceutical composition comprising pridopidine or a pharmaceutically acceptable salt thereof effective to treat the subject. The subject invention also provides a method of preventing or reducing retinal ganglion cell damage or loss in a subject, comprising administering to the subject a pharmaceutical composition comprising pridopidine or a pharmaceutically acceptable salt thereof effective to prevent or reduce retinal ganglion cell damage or loss in the subject.

The subject invention provides a method of treating a subject afflicted with a neurodegenerative eye disease comprising administering to the subject a pharmaceutical composition comprising pridopidine or a pharmaceutically acceptable salt thereof effective to provide neuroprotection to a retinal ganglion cell in the subject.

The subject invention provides a method of treating a subject afflicted with a neurodegenerative eye disease comprising administering to the subject a pharmaceutical composition comprising pridopidine or a pharmaceutically acceptable salt thereof and at least one of compounds 1-8 or pharmaceutically acceptable salt thereof:

(Compound 1)

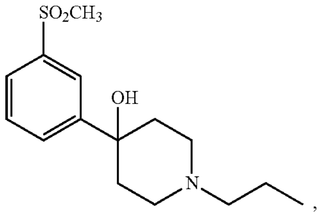

(Compound 2)

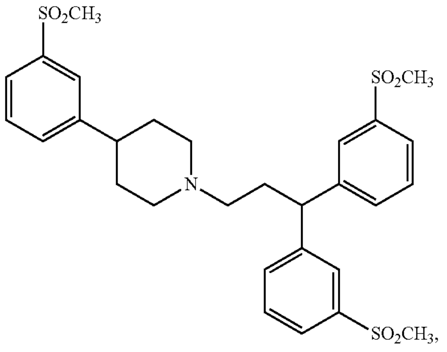

(Compound 3)

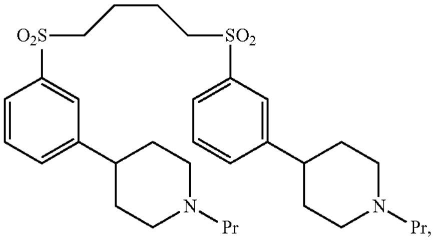

-continued (Compound 4)

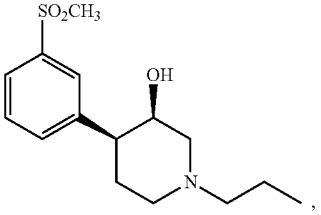

(Compound 5)

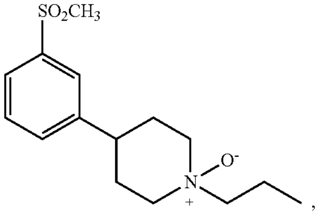

(Compound 6)

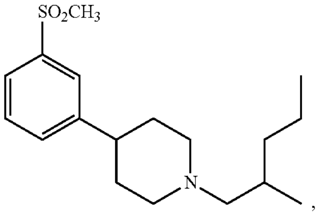

(Compound 7)

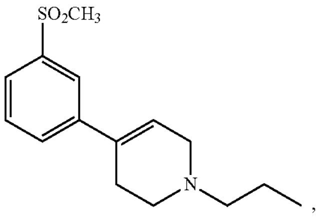

or (Compound 8)

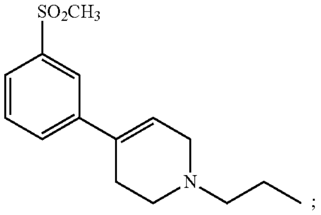

effective to provide neuroprotection to a retinal ganglion cell in the subject.

The subject invention also provides a pharmaceutical composition comprising an amount of pridopidine or a pharmaceutically acceptable salt thereof for treating a subject afflicted with a neurodegenerative eye disease.

The subject invention also provides a pharmaceutical composition comprising an amount of pridopidine or a pharmaceutically acceptable salt thereof and at least one compound of formula 1-8 or pharmaceutically acceptable salt thereof, for treating a subject afflicted with a neurodegenerative eye disease.

The subject invention also provides a pharmaceutical composition comprising pridopidine or a pharmaceutically acceptable salt thereof for use in a combination therapy together with a pharmaceutical composition comprising a second agent for the treatment of a neurodegenerative eye disease.

The subject invention also provides a pharmaceutical composition comprising an amount of pridopidine or a pharmaceutically acceptable salt thereof for use in treating a subject afflicted with a neurodegenerative eye disease as an add-on therapy or in combination with a second agent for the treatment of a neurodegenerative eye disease.

The subject invention also provides a pharmaceutical composition in a unit dosage form, useful in treating a subject afflicted with a neurodegenerative eye disease, which comprises an amount of pridopidine or pharmaceutically acceptable salt thereof, wherein the amount of said pridopidine in said composition is effective, upon administration to said subject of one or more of said unit dosage forms of said composition, to treat the subject.

The subject invention also provides a pharmaceutical composition in a unit dosage form, useful in treating a subject afflicted with a neurodegenerative eye disease, which comprises an amount of pridopidine or pharmaceutically acceptable salt thereof and at least one of compounds 1-8 or pharmaceutically acceptable salt thereof, wherein the amount of said pridopidine in said composition is effective, upon administration to said subject of one or more of said unit dosage forms of said composition, to treat the subject.

Further provided is pridopidine for use in treating a subject afflicted with a neurodegenerative eye disease.

Provided herein is pridopidine for the manufacture of a medicament for use in treating a subject afflicted with a neurodegenerative eye disease.

BRIEF DESCRIPTION OF THE FIGURES

FIG. 1: Schematic diagram of study design. Hypertonic saline injections were administered on days 0 and 7 of the experiment. Intraocular pressure (OP) was measured in both eyes on days 0,7,14,21,29,35 and 41. Animals were sacrificed on Day 41 and retinas collected for assessment.

FIG. 2: Presents average intraocular pressure measured in ocular hypertension (OHT) eye (OD—oculus dexter, right eye) and non-OHT control (OS, oculus sinister, left eye, dashed line) eye over 41 days of the study. TOP was elevated in the OD eye of all groups to the same extent [control (double distilled water, DDW), and pridopidine 3, 30 and 60 mg/kg], and remained high throughout the course of the study. Pridopidine treatment did not affect IOP in any of the groups.

FIG. 3: Diagram of regions of interest (ROI) collected from flat-mount retinas. Outline—flat-mounted retina; boxes—representative image location, FIG. 4: Presents pridopidine rescues Retinal Ganglion Cells (RGCs) in Morrison model for retinal neurodegeneration. Average RGC loss per treatment group, calculated as the difference between the OD and the OS eye. Over 40% of RGCs are lost in the control group treated with double distilled water (DDW) as control. Pridopidine at the 30 and 60 mg/kg doses significantly reduces RGC loss to 21% and 7%, respectively. Pridopidine 3 mg/kg shows a similar trend, reducing RGC loss to 25%. Data is mean±SEM. (DDWn=11, 3 mg/kg, n=8, 30 mg/kg, n=9, 60 mg/kg, n=10). *P<0.05, One-way ANOVA.

FIG. 5: Representative images of retinas from mice stained for RGCs with antibodies against the RGC-specific marker brain-specific homeobox/POU domain protein 3A (Brn-3a).

Food-deprived male Long Evans rats were treated with 3 mg/kg of $^{14}C$-labelled pridopidine free base, and radioactivity levels assayed at specific time points.

Figure 6:
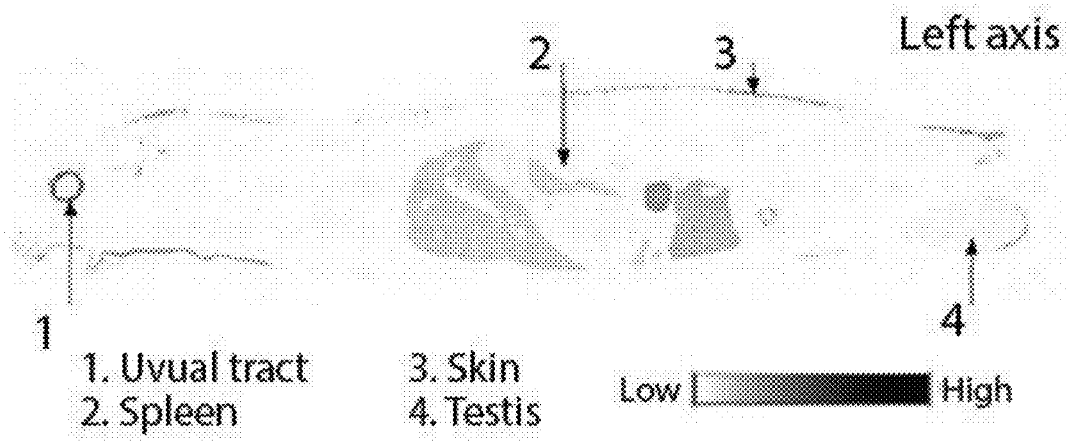
FIGS. 6-8: Pridopidine Binds Strongly to Melanin

FIG. 6: depicts that pridopidine binds strongly to melanin in uveal tract, spleen, skin and testes After 24 hours, a whole-body radioluminogram was acquired, showing high levels of $^{14}C$-labeled pridopidine in the highly pigmented uveal tract (1), spleen (2) and pigmented skin (3).

Figure 7:
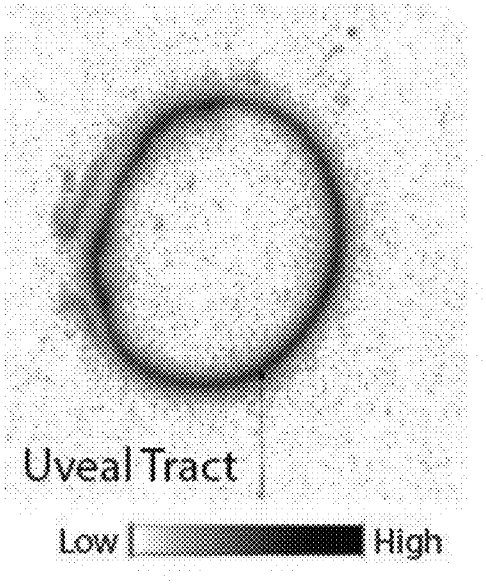

FIG. 7: depicts that pridopidine binds strongly to melanin in uveal tract. Magnified image of the uveal tract demonstrating high levels of $^{14}C$-labelled pridopidine.

Figure 8:
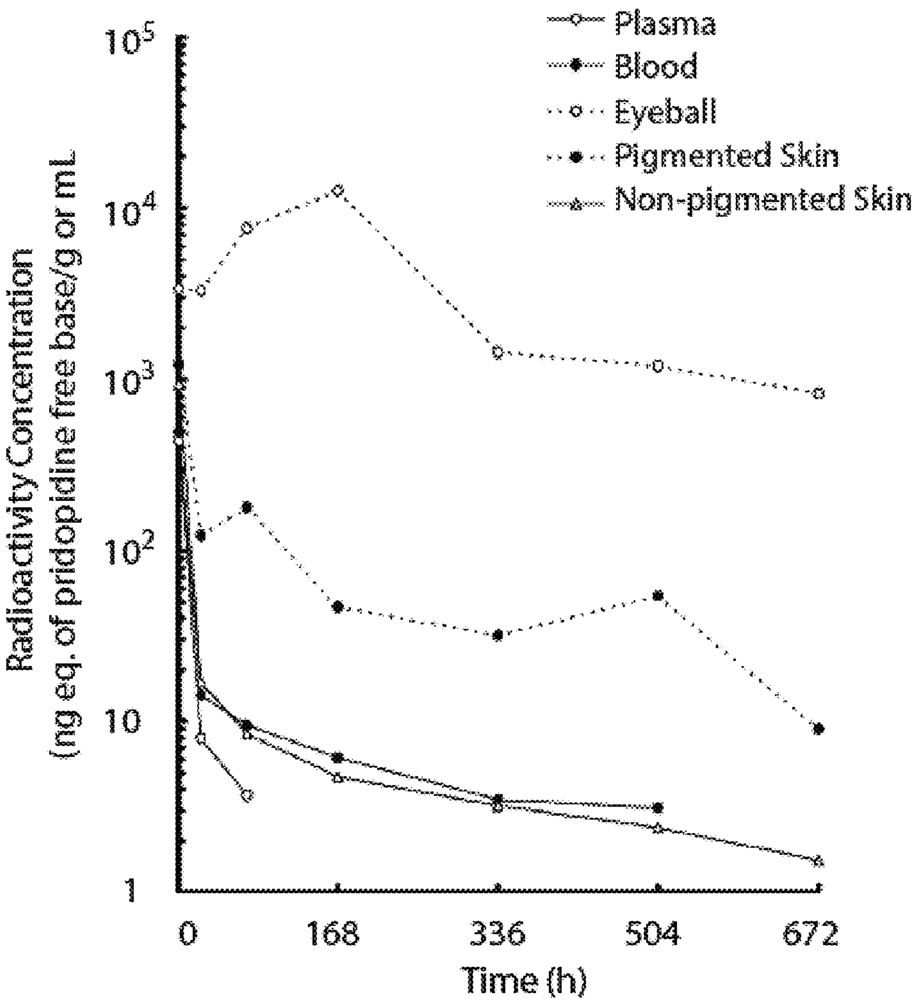

FIG. 8: Presents that pridopidine is retained in pigmented tissues. Relative levels of radioactivity were measured in different tissues over time. Each data point is the value of one animal. In plasma, radioactivity levels dropped significantly within 24 hours after administration, and are undetectable after 3 days. The highest level of radioactivity is recorded in the eyeball 168 hours (1 week) after administration, and remains high at 672 hours (4 weeks). Relatively high levels are also observed in pigmented skin, FIGS. 9-12: Pridopidine Effect on RGCs in Albino Rats FIG. 9: Schematic diagram of study design in laser coagulation model. Laser coagulation (LC) of episcleral veins was performed on albino Wistar rats on days 0 and 7 of the study. IOP was measured on days 0, 4, 7, 8 and 14. On day 14 animals were sacrificed and retina and optic nerves collected for further evaluation.

Figure 10:
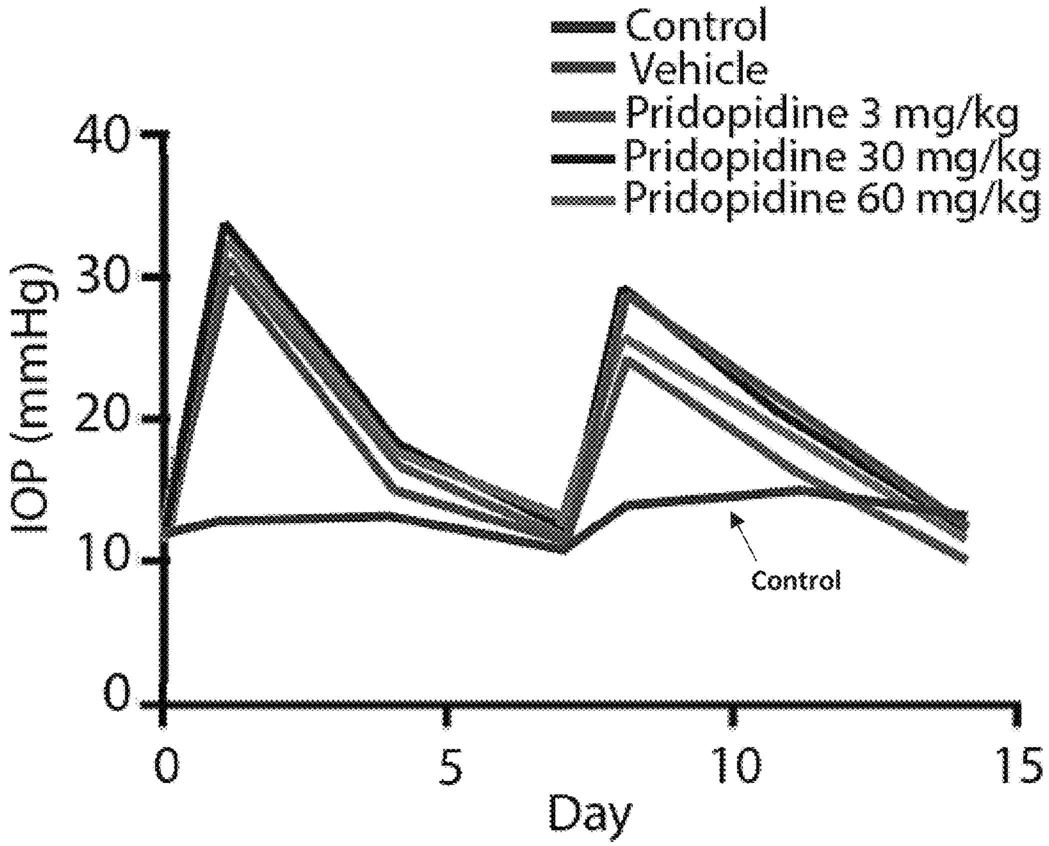

FIG. 10: IOP in different treatment groups at a given study time point (day 0/baseline, day 1, day 4, day 7, day 8, day 11, day 14). TOP is significantly increased in treated eyes following both LCs, and decreases back to normal after 7 days. Only eyes in which the cumulative IOP exceeded 125 mmHg, with no one TOP measurement above 55 mmHg were included in the analysis of RGC and optic nerve axon survival. This was done to exclude cases of retinal ischemia or cases in which the model failed to be established.

Figure 11:
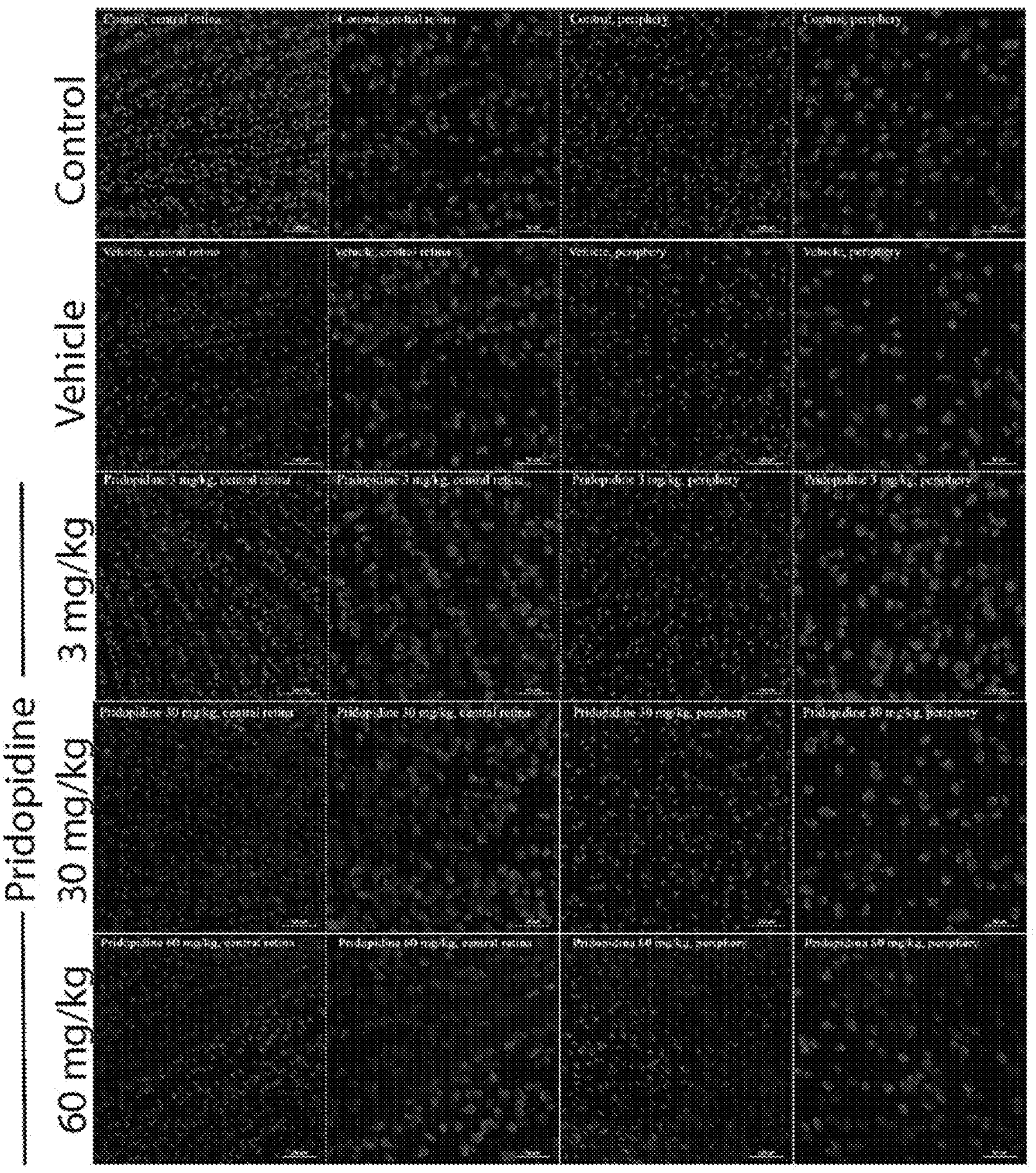

FIG. 11: Representative images of micrographs of RGCs stained for the specific RGC marker RNA-binding protein with multiple splicing (RBPMS). Images were acquired from the central part of retina (low and high magnifications) and the peripheral part of retina (low and high magnifications, respectively) from different treatment groups: contralateral control (healthy eye), vehicle, pridopidine 3 mg/kg, pridopidine 30 mg/kg, pridopidine 60 mg/kg. Scale bar in low magnification images is 100 μm, and in high magnification images is 50 μm.

Figure 12:
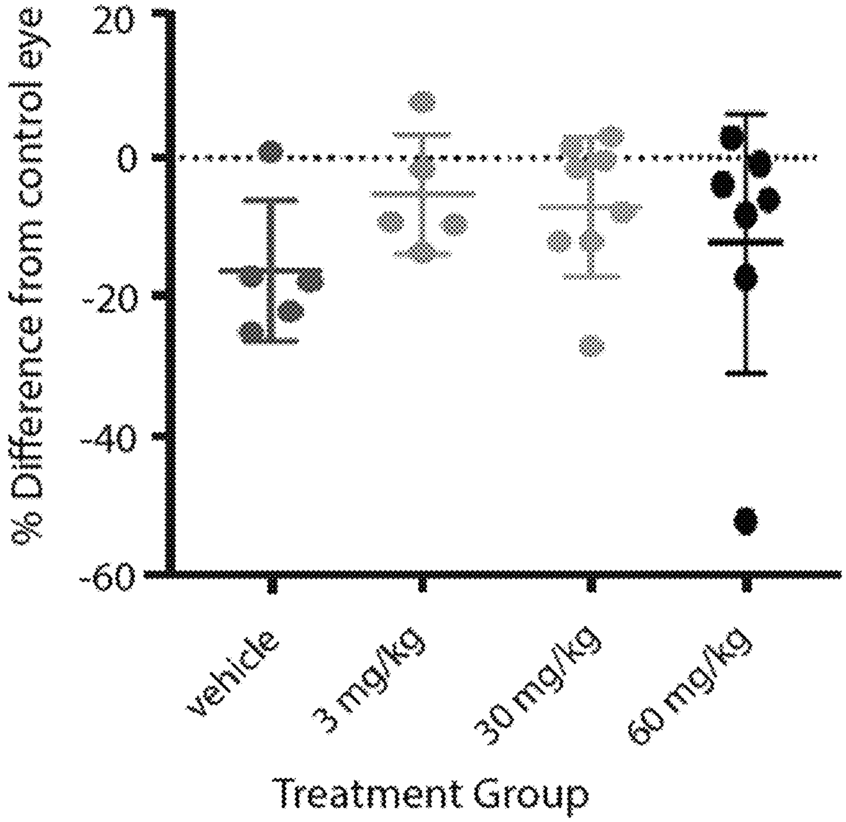

FIG. 12: Pridopidine rescues loss of RGC cells in LC model as measured by RBPMS-positive cells. RGC cells in LC eyes were compared to contralateral control eyes (without LC). In the vehicle-treated group, RGC numbers are decreased by 16.7% compared to the control eye. Pridopidine shows rescue of RGC cells. At the 3 mg/kg and 30 mg/kg pridopidine, RIC numbers in the right (LC) eye decrease only by 5.2% and 7.7% compared to the control left eyes, respectively, indicating a trend of a protective effect of pridopidine. In the 60 mg/kg group RGCs decrease by 13.9% compared to control eye. The data are presented as mean±SD. One-way ANOVA followed by Dunn's post hoc test. vehicle: n=6, 3 mg/kg n=5, 30 mg/kg n=9, 60 mg/kg n=7.

Figure 13:
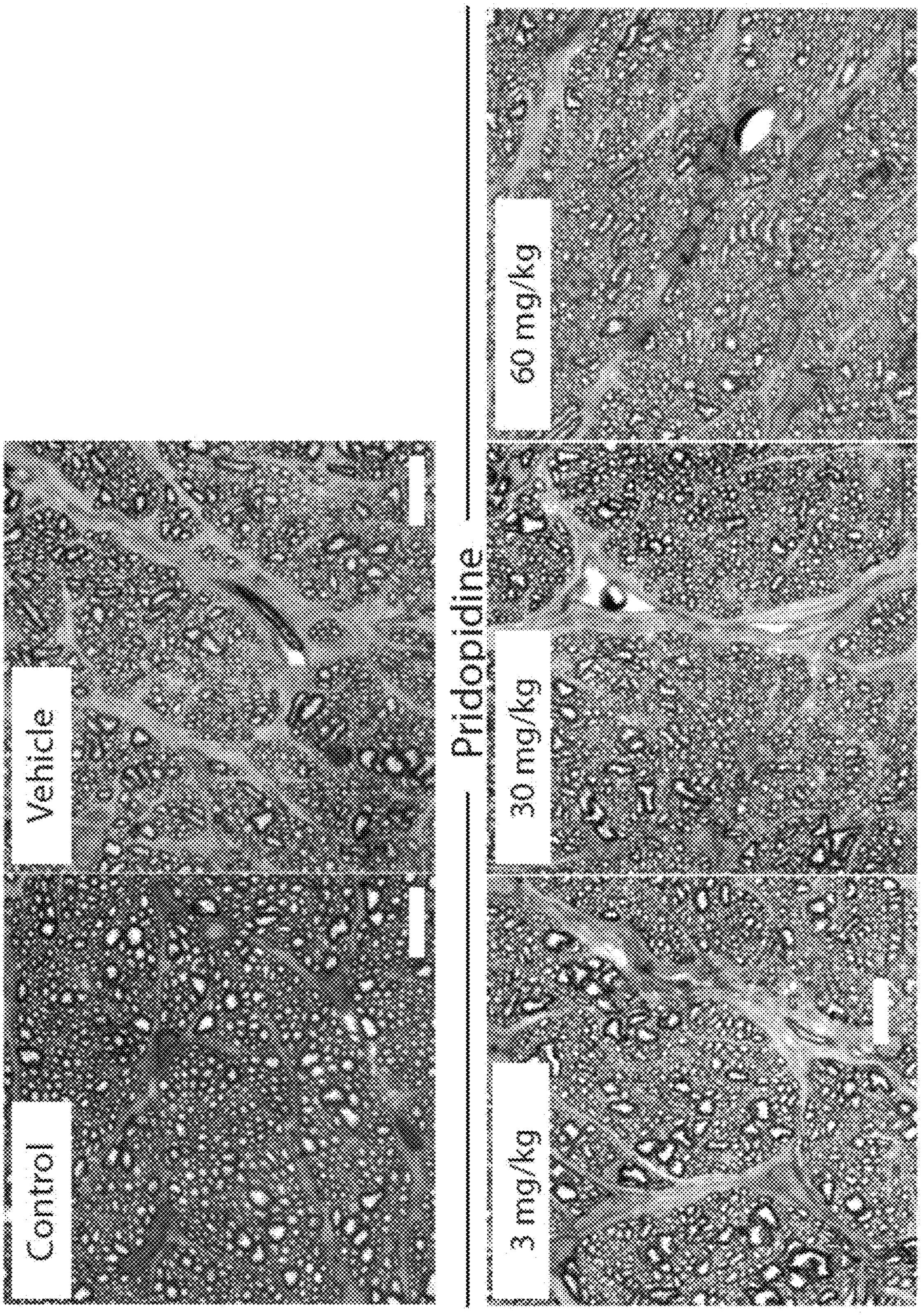
Figure 14:
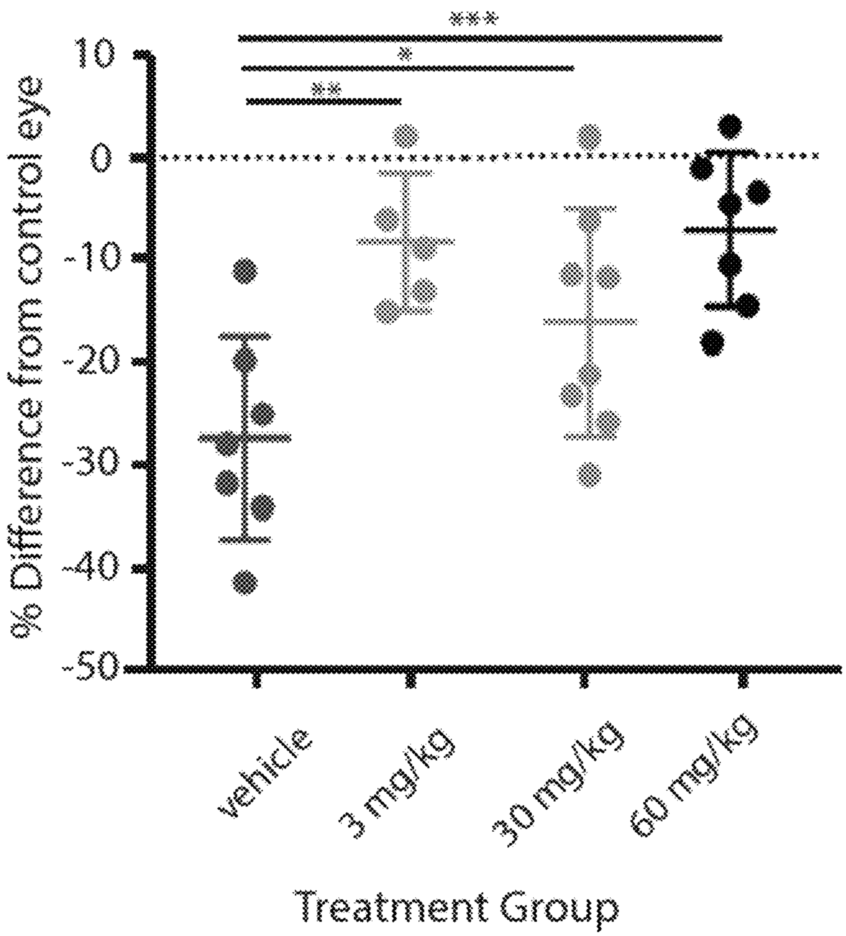

FIGS. 13-14: Pridopidine Rescues Optic Nerve Axons in Albino Rats

Neuroprotective preservation of visual function in glaucoma and other optic neuropathies depends not only on preservation of cell bodies, but also on maintaining connectivity between the eye and the brain. Connectivity is preserved by protecting RGC axons in the optic nerve.

FIG. 13: Representative micrographs of optic nerve sections acquired from semi-thin sections of optic nerves that were subjected to myelin enhancement staining. Scale bar in all images is 10 μm. Images were taken from the following animals: control, vehicle, pridopidine 3 mg/kg, pridopidine 30 mg/kg, pridopidine 60 mg/kg.

FIG. 14: Pridopidine rescues optic nerve axons in LC model. Data show % difference of optic nerve axons in the LC eyes from different treatment groups as compared to contralateral control eyes (without LC). In vehicle-treated eyes there was 27.5% loss of optic nerve axons in the LC eye compared to the control eye. Pridopidine 3 mg/kg, demonstrates a significant protection of axon loss showing only 8.6% loss of optic nerve axons in the LC eye vs. control eye, ($p=0.006$). At 30 ng/kg and 60 mg/kg pridopidine there was also a significant protective effect on optic nerve axons: 15% at the 30 mg/kg group ($p=0.04$) and 7.24%, at the 60 mg/kg group ($p=0.002$). The data are presented as mean±SD. 1-way ANOVA followed by Dunnett's post-hoc test, *$p<0.05$, $p<0.01$, *$p<0.005$. vehicle: n=6, 3 mg/kg: n=5, 30 mg/kg: n=9, 60 mg/kg: n=7.

Figures 15A, 15B:
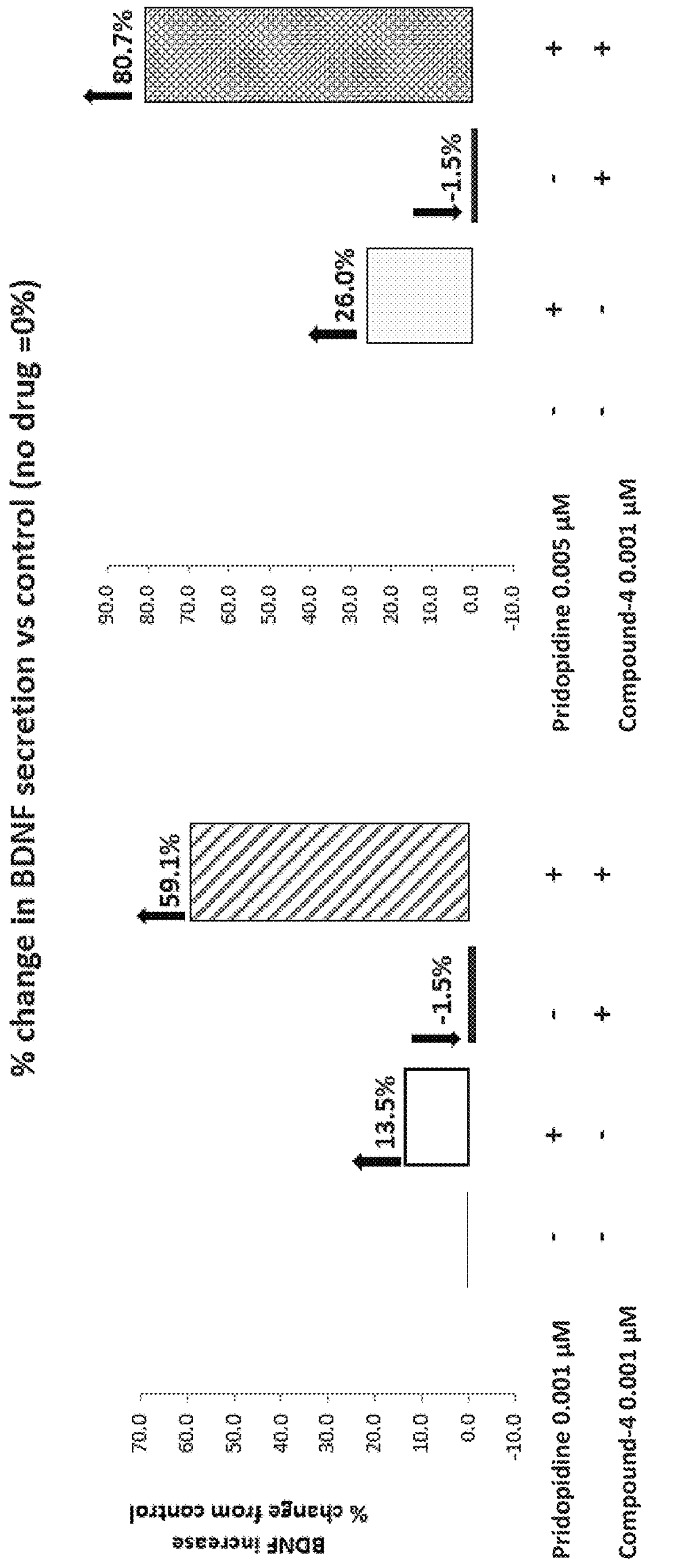

FIGS. 15A-15B: Synergistic effect of pridopidine and Compound 4 on BDNF Release from B104 cells. B104 neuroblastoma cells were incubated for 5 days with test compounds, and BDNF levels were assessed using in-situ ELISA. FIG. 15A: Pridopidine at a concentration of 0.001 μM and Compound 4 at a concentration of 0.001 μM. Pridopidine alone increased BDNF secretion by 13.5%. Compound 4 alone reduced BDNF secretion by −1.5%. Pridopidine and compound 4 together increased BDNF secretion by 59.1%, an effect which is greater than the added effect of both compounds administered on their own. FIG. 15B: Pridopidine at a concentration of 0.005 μM and Compound 4 at a concentration of 0.001 μM. Pridopidine alone increased BDNF secretion by 26.0%. Compound 4 alone reduced BDNF secretion by −1.5%. Pridopidine and compound 4 together increased BDNF secretion by 80.7%, an effect which is greater than the added effect of both compounds administered on their own.

Figure 16:
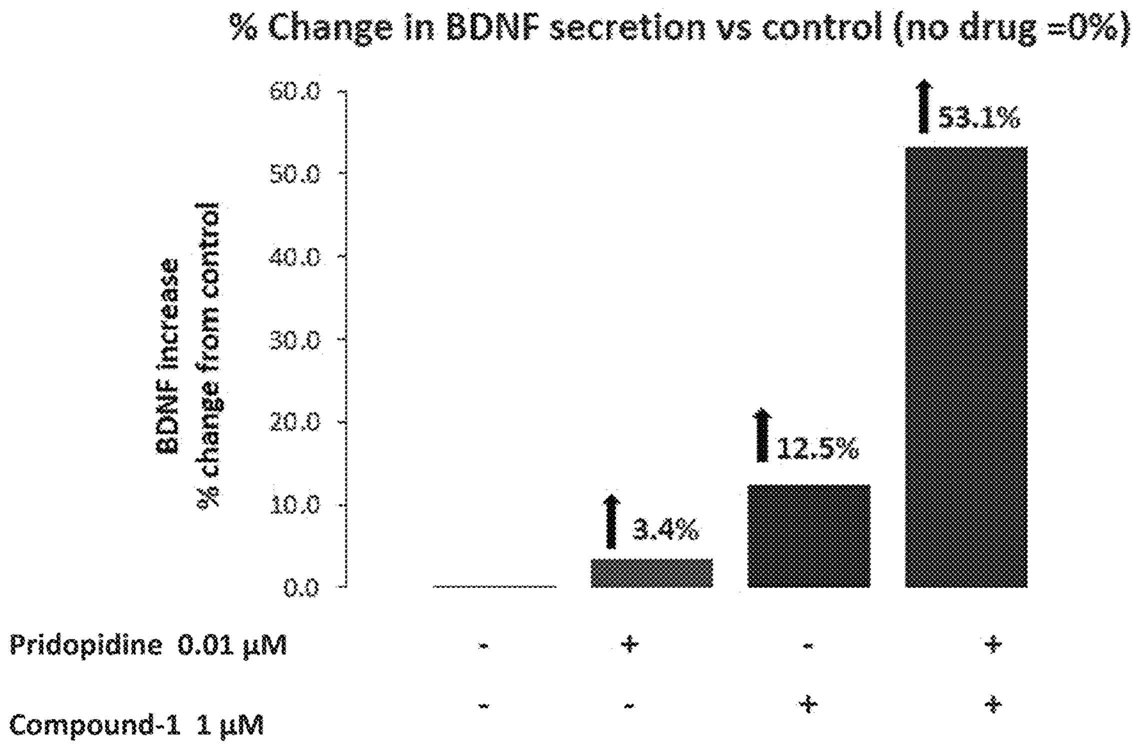

FIG. 16: Synergistic effect of pridopidine and Compound 1 on BDNF Release from B104 cells. B104 neuroblastoma cells were incubated for 5 days with test compounds, and BDNF levels were assessed using in-situ ELISA. Pridopidine at a concentration of 0.01 μM alone increased BDNF secretion by 3.4%. Compound 1 at a concentration of 1 μM alone increased BDNF secretion by 12.5%. Pridopidine and compound 1 together increased BDNF secretion by 53.1%, an effect which is greater than the added effect of both compounds administered on their own.

DETAILED DESCRIPTION OF THE INVENTION

The subject invention provides a method of treating a subject afflicted with a neurodegenerative eye disease comprising administering to the subject a pharmaceutical composition comprising pridopidine or a pharmaceutically acceptable salt thereof effective to treat the subject.

The subject invention provides a method of treating a subject afflicted with a neurodegenerative eye disease comprising administering to the subject a pharmaceutical composition comprising pridopidine or a pharmaceutically acceptable salt thereof and at least one of compounds 1-8 or pharmaceutically acceptable salt thereof effective to treat the subject.

The subject invention provides a method of treating, reducing or inhibiting a symptom of neurodegenerative eye disease in a subject afflicted with a neurodegenerative eye disease comprising administering to the subject a composition comprising pridopidine or pharmaceutically acceptable salt thereof.

The subject invention provides a method of treating, reducing or inhibiting a symptom of neurodegenerative eye disease in a subject afflicted with a neurodegenerative eye disease comprising administering to the subject a composition comprising pridopidine or pharmaceutically acceptable salt thereof and at least one of compounds 1-8 or pharmaceutically acceptable salt thereof.

In other embodiments the symptom is an optic nerve axon damage or loss. In other embodiments, the symptom is a retinal ganglion cell (RGC) loss or death. In other embodiments, the composition is effective to reduce or prevent optic nerve axon loss or damage in a subject. In other embodiments, the composition is effective to reduce or prevent a retinal ganglion cell (RGC) loss or death in a subject.

In other embodiments, the optic nerve axon loss is reduced by at least 3%, by at least 5%, by at least 10%, by at least 20%, by at least 30%, by at least 40% or by at least 50%. In other embodiments, the optic nerve axon loss is reduced by more than 50%, more than 60%, more than 70%, or more than 80%. In other embodiments, the composition is effective to protect an optic nerve axon from degeneration in the subject. In other embodiments, the axon degeneration is induced by elevated intraocular pressure.

In one embodiment, the administration of pridopidine or pharmaceutically acceptable salt thereof is effective to reduce or inhibit a symptom of the neurodegenerative eye disease in the subject.

In one embodiment, the administration of a composition comprising pridopidine or pharmaceutically acceptable salt thereof and at least one of compounds 1-8 or pharmaceutically acceptable salt thereof is effective to reduce or inhibit a symptom of the neurodegenerative eye disease in the subject.

In an embodiment, the neurodegenerative eye disease is selected from the group consisting of glaucoma, Age-related Macular Degeneration optic neuropathy, and retinitis pigmentosa. In another embodiment, the neurodegenerative eye disease refers to any disease affecting retinal ganglion cells, photoreceptors, other retinal neurons, and corneal nerves.

Diseases affecting retinal ganglion cells and their connections are optic neuropathies, and include glaucomatous optic neuropathy, also called glaucoma; inflammatory optic neuropathy, also called optic neuritis; ischemic optic neuropathy; toxic optic neuropathy; compressive optic neuropathy; infiltrative optic neuropathy; hereditary optic neuropathy; traumatic optic neuropathy; nutritional optic neuropathy; optic neuropathy from increased intracranial pressure, also called papilledema optic neuropathy; disc drusen optic neuropathy; autoimmune optic neuropathies; and other optic neuropathies. Each category of optic neuropathies may include subcategories, for example for ischemic optic neuropathy there is nonarteritic anterior ischemic optic neuropathy, arteritic anterior ischemic optic neuropathy, and posterior ischemic optic neuropathy.

In some embodiments, the neurodegenerative eye disease is glaucoma, including all clinical forms of glaucoma. For example, for glaucoma there is open-angle glaucoma and angle-closure glaucoma, and for each of those, there are sub-subcategories, for example, for open-angle glaucoma there is primary open-angle-glaucoma, pigmentary glaucoma, pseudoexfoliative glaucoma, neovascular glaucoma, steroid-induced glaucoma, normal-tension glaucoma, pressure-independent glaucoma, and many others.

Diseases affecting photoreceptors and other cells in the retina other than retinal ganglion cells include age-related macular degeneration (AMD), including wet and dry AMD; cystoid macular edema; central serous chorioretinopathy; macular pucker or macular hole: diabetic and nondiabetic macular edema; epiretinal membrane; all variants of retinitis pigmentosa and similar inherited or non-inherited retinal degenerations; retinal detachment; solar retinopathy; autoimmune retinopathy; retinal artery occlusions; retinal vein occlusions; diabetic retinopathy; infectious retinopathies; inflammation affecting the retina, including uveitis; degenerative retinal disorders from myopia; lattice degeneration.

Diseases affecting corneal nerves include infections, for example herpes viruses, leprosy, acanthamoeba, and fungi; toxic agents, for example topical anesthetics, preservative agents, and others; sensory neuropathies, for example trigeminal nerve disease or injury, hereditary or acquired polyneuropathies; corneal disease, for example corneal dystrophies, keratoconus, bullous keratopathy, and others; autoimmune diseases, for example Sjogren's syndrome; dry eyes; the effects of corneal surgery, for example after laser in situ keratomileusis (LASIK), corneal transplant, and others.

In one embodiment, the neurodegenerative eye disease is glaucoma. In another embodiment, the neurodegenerative eye disease is Wet Age-related Macular Degeneration ("Wet AMD") or Dry Age-related Macular Degeneration ("Dry AMD"). In a further embodiment, the neurodegenerative eye disease is Leber hereditary optic neuropathy (LHON).

In one embodiment, the symptom is retinal ganglion cell damage or retinal ganglion cell loss or optic nerve axon loss or damage.

In one embodiment, the method comprises reducing retinal ganglion cell loss or damage in the subject.

In one embodiment, the amount of pridopidine is effective to reduce or prevent retinal ganglion cell loss or damage in the subject. In another embodiment, the retinal ganglion cell loss is reduced by at least 3%, at least 5%, at least 10%, by at least 20%, by at least 30%, by at least 40% or by at least 50%. In a further embodiment, the retinal ganglion cell loss is reduced by more than 50%, more than 60%, more than 70%, or more than 80%.

In one embodiment, treating comprises improving retinal ganglion cell viability in the patient by more than 50%, more than 60%, more than 70%, or more than 80%.

In another embodiment, treating comprises reducing retinal ganglion cell loss in the patient by more than 50%, more than 60%, more than 70%, or more than 80%.

The subject invention also provides a method of preventing or reducing retinal ganglion cell damage or loss in a subject, comprising administering to the subject a pharmaceutical composition comprising pridopidine or a pharmaceutically acceptable salt thereof effective to prevent or reduce retinal ganglion cell damage or loss in the subject. In one embodiment, the composition is effective to improve retinal ganglion cell viability in a subject. In another embodiment, the composition is effective to protect a retinal ganglion cell from cell death in the subject. In some embodiments, the cell death is induced by elevated intraocular pressure.

The subject invention also provides a method of preventing or reducing retinal ganglion cell damage or loss in a subject, comprising administering to the subject a pharmaceutical composition comprising pridopidine or a pharmaceutically acceptable salt thereof and at least one of compounds 1-8 or pharmaceutically acceptable salt thereof effective to prevent or reduce retinal ganglion cell damage or loss in the subject. In one embodiment, the composition is effective to improve retinal ganglion cell viability in a subject. In another embodiment, the composition is effective to protect a retinal ganglion cell from cell death in the subject. In some embodiments, the cell death is induced by elevated intraocular pressure.

In one embodiment, the method comprises reducing optic nerve axon loss or damage in the subject.

In one embodiment, the pharmaceutical composition comprising pridopidine or a pharmaceutically acceptable salt thereof is effective to reduce or prevent optic nerve axon loss or damage in the subject. In another embodiment, the optic nerve axon loss is reduced by at least 3%, at least 5%, at least 10%, by at least 20%, by at least 30%, by at least 40% or by at least 50%. In a further embodiment, the optic nerve axon loss is reduced by more than 50%, more than 60%, more than 70%, or more than 80%.

In one embodiment, treating comprises improving optic nerve axon viability in the patient by more than 10%, more than 20%, more than 30%, more than 40%, more than 50%, more than 60%, more than 70%, or more than 80%.

In another embodiment, treating comprises reducing optic nerve axon loss in the patient by more than 10%, more than 20%, more than 30%, more than 40%, more than 50%, more than 60%, more than 70%, or more than 80%.

The subject invention also provides a method of preventing or reducing optic nerve axon damage or loss in a subject, comprising administering to the subject a pharmaceutical composition comprising pridopidine or a pharmaceutically acceptable salt thereof effective to prevent or reduce optic nerve axon damage or loss in the subject. In one embodiment, the composition is effective to improve optic nerve axon viability in a subject. In another embodiment, the composition is effective to protect an optic nerve axon from cell death in the subject. In some embodiments, the cell death is induced by elevated intraocular pressure.

The subject invention also provides a method of preventing or reducing optic nerve axon damage or loss in a subject, comprising administering to the subject a pharmaceutical composition comprising pridopidine or a pharmaceutically acceptable salt thereof and at least one of compounds 1-8 or pharmaceutically acceptable salt thereof effective to prevent or reduce optic nerve axon damage or loss in the subject. In one embodiment, the composition is effective to improve optic nerve axon viability in a subject. In another embodiment, the composition is effective to protect an optic nerve axon from cell death in the subject. In some embodiments, the cell death is induced by elevated intraocular pressure.

In another embodiment, treating comprises slowing progression of the neurodegenerative disease of the eye in the subject. In some embodiments, the treating comprises slowing progression of visual field loss towards blindness in a patient afflicted with glaucoma. In some embodiments, treating comprises preventing blindness in a patient afflicted with glaucoma.

In one embodiment, pridopidine is pridopidine hydrochloride.

For the methods and use disclosed herein, the route of administration can be, e.g., oral. Routes of administration can also be classified by whether the effect is local (e.g., in topical administration) or systemic (e.g., in enteral or parenteral administration). "Local administration" as used herein shall mean administration of a compound or composition directly to where its action is desired, and specifically excludes systemic administration. "Topical administration" of a compound or composition as used herein shall mean application of the compound or composition to body surfaces such as the skin or mucous membranes such as eyes. "Ocular administration" as used herein shall mean application of a compound or composition to the eye of a subject or to the skin around the eye (periocular skin) or the mucosa around the eye, specifically the conjunctiva of a subject, i.e., local administration. Examples of ocular administration include topical administration directly to the eye, topical application to the eye lid or injection into a portion of the eye or eye socket. In addition, an "ocular pharmaceutical composition" as used herein means a pharmaceutical composition formulated for ocular administration. The amount of pridopidine and the pharmaceutical compositions of the present invention may be administered by oral administration, topical administration, systemic administration, local administration, or ocular administration. In other embodiments, the composition described herein are administered orally, topically, intraocularly, periocularly or ocularly. In other embodiments, the composition described herein is administered by an eye drop application to the conjunctiva.

In one embodiment, the pharmaceutical composition comprising pridopidine or a pharmaceutically acceptable salt thereof is administered via systemic administration. In some embodiments, the pharmaceutical composition is administered via oral administration. In another embodiment, the pharmaceutical composition is administered in the form of an aerosol, an inhalable powder, an injectable, a liquid, a gel, a cream, a solid, a capsule or a tablet. In other embodiments, the composition described herein is administered orally, topically, intravitreally, intraocularly, periocularly or ocularly. In other embodiments, the composition described herein is administered by an eye drop application to the conjunctiva.

In one embodiment, the pharmaceutical composition comprising pridopidine or a pharmaceutically acceptable salt thereof and at least one of compounds 1-8 or pharmaceutically acceptable salt thereof is administered via systemic administration. In some embodiments, the pharmaceutical composition is administered via oral administration. In another embodiment, the pharmaceutical composition is administered in the form of an aerosol, an inhalable powder, an injectable, a liquid, a gel, a cream, a solid, a capsule or a tablet. In other embodiments, the composition described herein is administered orally, topically, intraocularly, intravitreally, periocularly or ocularly. In other embodiments, the composition described herein is administered by an eye drop application to the conjunctiva.

In one embodiment, the pharmaceutical composition described herein is administered via local administration to the eye. In another embodiment, the pridopidine is administered via topical administration. In a further embodiment, the pridopidine is administered via intraocular, periocular, or ocular administration. In some embodiments, the pridopidine is administered in the form of a liquid, a gel, a cream or a contact lens.

In another embodiment, the pharmaceutical composition described herein is administered directly to the eye of a subject, for example as eye drops, an intraocular depot injection, eye gels, a tablet inserted into the conjunctiva, or a lens loaded with pridopidine. In an embodiment, pridopidine hydrochloride is administered to the eye of the subject.

In one embodiment, the pharmaceutical composition described herein is part of a formulation suitable to be administered by ocular drops. The ocular drops can be in the form of a liquid or a gel, preferably in the form of a liquid. When the pharmaceutical composition is administered topically in the form of a liquid or gel to the eye, a lower amount of pridopidine is required to produce the same clinical effect as systemic administration of pridopidine.

In one embodiment, the amount of pridopidine administered systemically is 22.5 mg/day-315 mg/day, 90 mg/day-315 mg/day, 90-250 mg/day, or 90-180 mg/day. In another embodiment, the amount of pridopidine administered is about 22.5 mg/day, about 45 mg/day, about 67.5 mg/day, about 90 mg/day, about 100 mg/day, about 112.5 mg/day, about 125 mg/day, about 135 trig/day, about 150 mg/day, about 180 mg/day, about 200 mg/day, about 225 mg/day, about 250 mg/day, or about 315 mg/day. In other embodiments, the composition comprising pridopidine or pharmaceutically acceptable salt thereof is administered in a daily dose comprising an amount of pridopidine between 22.5 mg/day-315 mg/day. In other embodiments, the composition comprising pridopidine or pharmaceutically acceptable salt thereof and at least one of compounds 1-8 or pharmaceutically acceptable salt thereof is administered in a daily dose comprising an amount of pridopidine between 22.5 mg/day-315 mg/day.

In one embodiment, the amount of pridopidine administered systemically in a dose is about 22.5 mg, about 45 mg, about 67.5 mg, about 90 mg, about 100 mg, about 112.5 mg, about 125 mg, about 135 mg, about 150 mg, about 180 mg, about 200 mg, about 250 mg, or about 315 mg. In another embodiment, the pharmaceutical composition described herein is administered directly to the eye of a subject. In some embodiments, pharmaceutical composition is formulated for direct administration to the eye, for example topical administration to the eye, for example as eye drops, and the pridopidine is prepared in a dose range of 0.1 mg to 50 mg, or 0.2 mg to 20 mg.

In one embodiment, the amount of pridopidine administered locally is 0.1 mg/day-50 mg/day or 0.2 mg/day 20 mg/day. In another embodiment, the amount of pridopidine administered locally in a dose is 0.1 mg-50 mg or 0.2 mg-20 mg.

In one embodiment the pharmaceutical composition described herein is administered periodically.

In one embodiment, the pharmaceutical composition described herein is administered daily.

In another embodiment, the pharmaceutical composition described herein is administered more often than once daily or less often than once daily. In one embodiment, the pharmaceutical composition described herein is administered more often than once daily, for example twice or thrice daily. In another embodiment, the pharmaceutical composition described herein is administered less often than once daily, for example, every other day or weekly.

In one embodiment, the periodic administration of the pharmaceutical composition described herein continues for at least 3 days, more than 30 days, more than 42 days, 8 weeks or more, at least 12 weeks, at least 24 weeks, more than 24 weeks, or 6 months or more. In some embodiments, for example, in the treatment of a subject with glaucoma, the treatment is a chronic treatment, with periodic administration of the pharmaceutical composition described herein for more than 12 months, more than 18 months, more than 24 months.

In one embodiment, the subject is a human patient.

In one embodiment, the method further comprises the administration of a second agent for the treatment of the neurodegenerative eye disease. In another embodiment, the second agent is a p-adrenergic antagonist, adrenergic agonist, parasympathomimetic agonist prostaglandin analog, or carbonic anhydrase inhibitor.

In another embodiment, the second agent reduces elevated intraocular pressure in a subject. In a further embodiment, the second agent is a prostaglandin agonist, a beta blocker, a carbonic anhydrase inhibitor, an alpha agonist, or a combination thereof. In an additional embodiment, the second agent is latanoprost, bimatoprost, travoprost ophthalmic, unoprostone ophthalmic, tafluprost, Betaxolol ophthalmic, Carteolol, timolol, levobunolol, metipranolol, Dorzolamide, brinzolamide, acetazol amide, methazolamide, brimonidine, Apraclonidine, or a combination thereof.

In one embodiment, the subject is administered a fixed-dose combination comprising the pharmaceutical composition described herein and the second agent.

In one embodiment, the package further comprising a second pharmaceutical composition comprising an amount of a second agent for the treatment of a neurodegenerative eye disease, wherein the instructions provide for use of the first and second pharmaceutical compositions together to treat a subject afflicted with a neurodegenerative eye disease.

In one embodiment, the amount of pridopidine and the amount of the second agent are prepared to be administered simultaneously, contemporaneously or concomitantly.

The subject invention also provides a pharmaceutical composition comprising pridopidine or a pharmaceutical acceptable salt thereof for treating a subject afflicted with a neurodegenerative eye disease.

The subject invention also provides a pharmaceutical composition comprising pridopidine or a pharmaceutical acceptable salt thereof and at least one of compounds 1-8 or pharmaceutically acceptable salt thereof for treating a subject afflicted with a neurodegenerative eye disease.

In one embodiment, the pharmaceutical composition further comprising an amount of a second agent for the treatment of a neurodegenerative eye disease.

In one embodiment, the pharmaceutical composition comprising pridopidine or pharmaceutically acceptable salt thereof and the second agent are prepared to be administered simultaneously, contemporaneously or concomitantly.

In one embodiment, the pharmaceutical composition comprising pridopidine or pharmaceutically acceptable salt thereof and at least one of compounds 1-8 or pharmaceutically acceptable salt thereof and the second agent are prepared to be administered simultaneously, contemporaneously or concomitantly.

The subject invention also provides a pharmaceutical composition comprising pridopidine for use in a combination therapy together with a pharmaceutical composition comprising a second agent for the treatment of a neurodegenerative eye disease.

The subject invention also provides a pharmaceutical composition comprising an amount of pridopidine or pharmaceutically acceptable salt thereof for use in treating a subject afflicted with a neurodegenerative eye disease as an add-on therapy or in combination with a second agent for the treatment of a neurodegenerative eye disease.

The subject invention also provides a pharmaceutical composition comprising an amount of pridopidine or pharmaceutically acceptable salt thereof and at least one of compounds 1-8 or pharmaceutically acceptable salt thereof for use in treating a subject afflicted with a neurodegenerative eye disease as an add-on therapy or in combination with a second agent for the treatment of a neurodegenerative eye disease.

In one embodiment, the amount of pridopidine in the pharmaceutical composition is about 22.5 mg, about 45 mg, about 67.5, mg, about 90 mg, about 100 mg, about 112.5 mg, about 125 mg, about 135 mg, about 150 mg, about 180 mg, about 200 mg, about 250 mg, or about 315 mg. In one embodiment, the amount of pridopidine in the pharmaceutical composition is 0.1 mg to 50 mg, or 0.2 mg to 20 mg.

In one embodiment, the dose of pridopidine in the pharmaceutical composition is measured as amount of pridopidine per weight of the subject. In another embodiment, the dose is between 1-100 mg/kg. In another embodiment, the dose is between 1-10, 20-50 or 50-100 mg/kg. In another embodiment, the dose is 3, 10, 30 or 60 mg/kg. The subject invention also provides a pharmaceutical composition in a unit dosage form, useful in treating a subject afflicted with a neurodegenerative eye disease, which comprises an amount of pridopidine or pharmaceutically acceptable salt thereof, wherein the amount of said pridopidine in said composition is effective, upon administration to said subject of one or more of said unit dosage forms of said composition, to treat the subject.

The invention also provides an ocular pharmaceutical composition comprising an amount of pridopidine and a pharmaceutically acceptable excipient suitable for administration to the eye. In one embodiment, the ocular pharmaceutical composition further comprising a second agent for the treatment of the neurodegenerative eye disease. In one embodiment, the second agent for the treatment of the neurodegenerative eye disease is an anti-glaucoma agent.

In another embodiment, the amount of pridopidine in the ocular pharmaceutical composition is 0.1 mg to 50 mg, or 0.2 mg to 20 mg.

In one embodiment, the ocular pharmaceutical composition is in the form of a liquid. In some embodiments, the concentration of pridopidine in the ocular pharmaceutical composition is from 0.0001 to 10.0 w/v %, 0.001 to 5 w/v %, 0.01 to 1 w/v %, 0.1% to 10 w/v %.

The invention also provides the ocular pharmaceutical composition for use in treating a neurodegenerative eye disease in a subject.

The invention further provides an eye drop comprising the pharmaceutical composition. The invention additionally provides a container comprising eye drops and the pharmaceutical composition.

The invention also provides an eye drop or a container comprising eye drops for use in the methods of this invention.

Further provided is pridopidine or a pharmaceutically acceptable salt thereof for use in treating a subject afflicted with a neurodegenerative eye disease.

Further provided is pridopidine or a pharmaceutically acceptable salt thereof and at least one of compounds 1-8 or pharmaceutically acceptable salt thereof for use in treating a subject afflicted with a neurodegenerative eye disease.

Provided herein is pridopidine for the manufacture of a medicament for use in treating a subject afflicted with a neurodegenerative eye disease.

Terms

As used herein, and unless stated otherwise, each of the following terms shall have the definition set forth below.

As used herein, "pridopidine" means pridopidine base or a pharmaceutically acceptable salt thereof, as well as derivatives, for example deuterium-enriched version of pridopidine and salts.

A "salt thereof" is a salt of the instant compounds which have been modified by making acid or base salts of the compounds. The term "pharmaceutically acceptable salt" in this respect, refers to the relatively non-toxic, inorganic and organic acid or base addition salts of compounds of the present invention. For example, one means of preparing such a salt is by treating a compound of the present invention with an inorganic base.

"A neurodegenerative eye disease" as used herein is a disease which involves degeneration of neurosensory cells in the eye and/or of the optic nerve, including specifically retinal cells and/or their axons. Neurosensory cells include retinal ganglion cells, optic nerve axon, retinal pigment epithelium cells, cones, rods, and all other neuronal or glial cell types of the retina. Neurodegenerative eye diseases are exemplified by glaucoma, age-related macular degeneration (AMD), including wet and dry AMD, all variants of retinitis pigmentosa, optic neuropathy, including but not limited to ischemic optic neuropathy (ION), hereditary Leber hereditary optic neuropathy (LHON), and retinopathies including for example Stargardt's retinopathy. Neurodegenerative eye diseases are exemplified by diseases of neurons of the eye and their connections, as exemplified by diseases affecting retinal ganglion cells, photoreceptors, other retinal neurons, and corneal nerves.

Diseases affecting retinal ganglion cells and their connections are optic neuropathies, and include glaucomatous optic neuropathy, also called glaucoma; inflammatory optic neuropathy, also called optic neuritis; ischemic optic neuropathy; toxic optic neuropathy; compressive optic neuropathy; infiltrative optic neuropathy; hereditary optic neuropathy; traumatic optic neuropathy; nutritional optic neuropathy; optic neuropathy from increased intracranial pressure, also called papilledema optic neuropathy; disc drusen optic neuropathy; autoimmune optic neuropathies; and other optic neuropathies. Each category of optic neuropathies may include subcategories, for example for ischemic optic neuropathy there is nonarteritic anterior ischemic optic neuropathy, arteritic anterior ischemic optic neuropathy, and posterior ischemic optic neuropathy.

In some embodiments, the neurodegenerative eye disease is glaucoma, including all clinical forms of glaucoma. For example, for glaucoma there is open-angle glaucoma and angle-closure glaucoma, and for each of those, there are sub-subcategories, for example, for open-angle glaucoma there is primary open-angle-glaucoma, pigmentary glaucoma, pseudoexfoliative glaucoma, neovascular glaucoma, steroid-induced glaucoma, normal-tension glaucoma, pressure-independent glaucoma, and many others. In some embodiments, the neurodegenerative eye disease is glaucoma, including all clinical forms of glaucoma, for example, primary glaucoma or secondary glaucoma. A primary glaucoma is for example, primary open angle glaucoma (POAG), normal-tension glaucoma (NTG), primary angle-closure glaucoma (PACG), acute angle-closure glaucoma (AACG) and angle-closure glaucoma (ACG). A secondary glaucoma is for example, pseudoexfoliation glaucoma, pigmentary glaucoma, neovascular glaucoma, steroid-induced glaucoma, and treatment refractory glaucoma.

Diseases affecting photoreceptors and other cells in the retina other than retinal ganglion cells include age-related macular degeneration (AMD), including wet and dry AMD; cystoid macular edema; central serous chorioretinopathy; macular pucker or macular hole; diabetic and nondiabetic macular edema; epiretinal membrane; all variants of retinitis pigmentosa and similar inherited or non-inherited retinal degenerations; retinal detachment; solar retinopathy; autoimmune retinopathy; retinal artery occlusions; retinal vein occlusions; diabetic retinopathy; infectious retinopathies; inflammation affecting the retina, including uveitis; degenerative retinal disorders from myopia; lattice degeneration.

Diseases affecting corneal nerves include infections, for example herpes viruses, leprosy, acanthamoeba, and fungi; toxic agents, for example topical anesthetics, preservative agents, and others; sensory neuropathies, for example trigeminal nerve disease or injury, hereditary or acquired polyneuropathies; corneal disease, for example corneal dystrophies, keratoconus, bullous keratopathy, and others; autoimmune diseases, for example Sjogren's syndrome; dry eyes; the effects of corneal surgery, for example after laser in situ keratomileusis (LASIK), corneal transplant, and others.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine hydrochloride, the weight of the salt form necessary to provide a dose of 90 mg pridopidine would he greater than 90 mg due to the presence of the salt.

As used herein, a "unit dose", "unit doses" and "unit dosage form(s)" mean a single drug administration entity/entities.

As used herein, "about" in the context of a numerical value or range means±10% of the numerical value or range recited or claimed.

As used herein, "effective" when referring to an amount of pridopidine refers to the quantity of pridopidine that is sufficient to yield a desired therapeutic response. Efficacy can be measured by e.g., a reduced retinal ganglion cell number or optic nerve axon loss or damage.

"Administering to the subject" or "administering to the (human) patient" means the giving of, dispensing of, or application of medicines, drugs, or remedies to a subject/patient to relieve, cure, or reduce the symptoms associated with a condition, e.g., a pathological condition. The administration can be periodic administration. As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

As used herein, "a pharmaceutically acceptable excipient suitable for administration to the eye" includes any excipient that is known to be or expected to be suitable for administration directly to the eye.

Excipients (or additives) that are usually used in formulating ocular drops can be used together with pridopidine. Excipients may include preservatives, including quaternary ammonium salts such as benzalkonium chloride, benzethonium chloride and the like; cationic compounds such as chlorhexidine gluconate and the like; p-hydroxybenzoates such as methyl p-hydroxybenzoate, propyl p-hydroxybenzoate and the like; alcohol compounds such as chlorobutanol, benzyl alcohol and the like; sodium dehydroacetate; thimerosal; sorbic acid; and the like (U.S. Pat. No. 6,114,319). The formulation suitable to be administered by ocular drops may include a buffer, such as acetates such as sodium acetate and the like, phosphates such as sodium dihydrogenphosphate, disodium hydrogenphosphate, potassium dihydrogenphosphate, dipotassium hydrogenphosphate and the like, aminocaproic acid, amino acid salts such as sodium glutamate and the like, boric acid and salt thereof, citric acid and salt thereof, and the like (U.S. Pat. No. 6,114,319). The fonnulation suitable to be administered by ocular drops may include excipients, such as a stabilizer, an antioxidant, a pH adjusting agent, a chelating agent, a thickener and the like (U.S. Pat. No. 6,114,319). Examples of the antioxidant include ascorbic acid and salt thereof, sodium thiosulfate, sodium hydrogensulfite, tocopherol, sodium thiosulfate, sodium hydrogensulfite, pyruvic acid and salt thereof, and the like (U.S. Pat. No. 6,114,319). Examples of chelating agent include sodium edetate, citric acid and salt thereof, and the like (U.S. Pat. No. 6,114,319). Examples of the pH adjusting agent include hydrochloric acid, phosphoric acid, acetic acid, sodium hydroxide, sodium hydrogencarbonate, potassium hydroxide, sodium carbonate, sulfuric acid, aqueous ammonia and the like (U.S. Pat. No. 6,114,319). The pH of the formulation suitable for administration by ocular drops may be at any point within an ophthalmologically acceptable range, for example, between pH 5.0 and pH 8.0. When pridopidine is to be administered by ocular drops or eye drops, it is preferable to prepare the formulation so that the concentration of pridopidine is from 0,0001 to 10.0 w/v %.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention. Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Composition for Use in the Methods of this Invention:

In some embodiments the methods of this invention make use of a pharmaceutical composition comprising pridopidine or pharmaceutically acceptable salt thereof. In some embodiments the methods of this invention make use of a pharmaceutical composition comprising pridopidine or pharmaceutically acceptable salt thereof and at least one of compounds 1-8

(Compound 1)

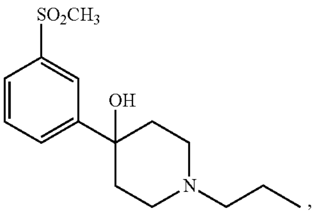

-continued (Compound 2)

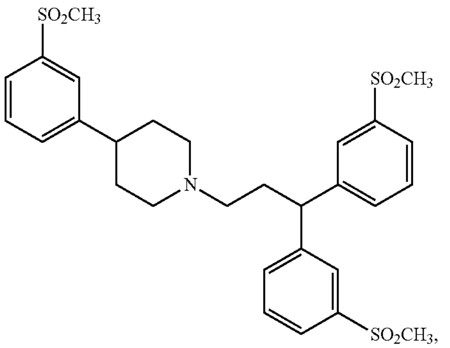

(Compound 3)

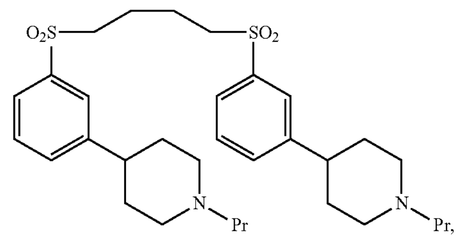

(Compound 4)

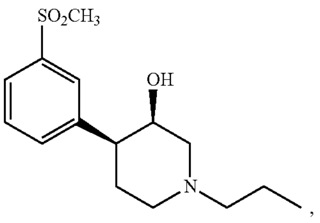

(Compound 5)

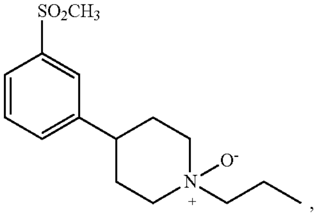

(Compound 6)

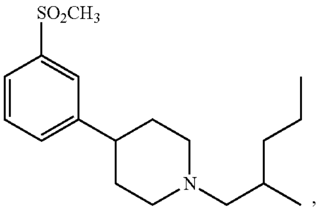

(Compound 7)

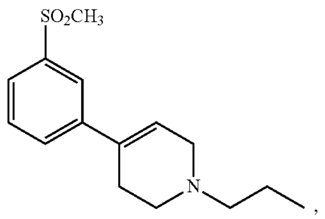

or

-continued (Compound 8)

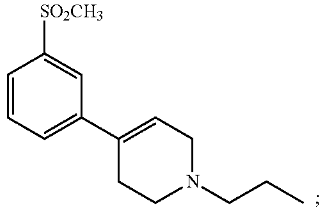

or pharmaceutically acceptable salt thereof.

In other embodiments the methods of this invention make use of a pharmaceutical composition comprising pridopidine or pharmaceutically acceptable salt thereof and compound 1 or pharmaceutically acceptable salt thereof.

In other embodiments the methods of this invention make use of a pharmaceutical composition comprising pridopidine or pharmaceutically acceptable salt thereof and compound 2 or pharmaceutically acceptable salt thereof.

In other embodiments the methods of this invention make use of a pharmaceutical composition comprising pridopidine or pharmaceutically acceptable salt thereof and compound 3 or pharmaceutically acceptable salt thereof.

In other embodiments the methods of this invention make use of a pharmaceutical composition comprising pridopidine or pharmaceutically acceptable salt thereof and compound 4 or pharmaceutically acceptable salt thereof.

In other embodiments the methods of this invention make use of a pharmaceutical composition comprising pridopidine or pharmaceutically acceptable salt thereof and compound 5 or pharmaceutically acceptable salt thereof.

In other embodiments the methods of this invention make use of a pharmaceutical composition comprising pridopidine or pharmaceutically acceptable salt thereof and compound 6 or pharmaceutically acceptable salt thereof.

In other embodiments the methods of this invention make use of a pharmaceutical composition comprising pridopidine or pharmaceutically acceptable salt thereof and compound 7 or pharmaceutically acceptable salt thereof.

In other embodiments the methods of this invention make use of a pharmaceutical composition comprising pridopidine or pharmaceutically acceptable salt thereof and compound 8 or pharmaceutically acceptable salt thereof.

In other embodiments the methods of this invention make use of a pharmaceutical composition comprising pridopidine or a pharmaceutically acceptable salt thereof and at least one of compound 1, compound 4, pharmaceutically acceptable salt thereof or combination thereof.

In other embodiments the methods of this invention make use of a pharmaceutical composition comprising pridopidine or a pharmaceutically acceptable salt thereof and compound 1 or pharmaceutically acceptable salt thereof.

In other embodiments the methods of this invention make use of a pharmaceutical composition comprising pridopidine or a pharmaceutically acceptable salt thereof and compound 4 or pharmaceutically acceptable salt thereof.

In other embodiments the methods of this invention make use of a pharmaceutical composition comprising pridopidine or a pharmaceutically acceptable salt thereof, compound 1 and compound 4 or pharmaceutically acceptable salt thereof.

In other embodiments the methods of this invention make use of a pharmaceutical composition comprising pridopidine salt, wherein the salt is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

In other embodiments the methods of this invention make use of a pharmaceutical composition comprising at least one of compounds 1-8 salt, wherein the salt is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

In other embodiments the methods of this invention make use of a pharmaceutical composition comprising pridopidine or pharmaceutically acceptable salt thereof and at least one of compounds 1-8 or pharmaceutically acceptable salt thereof, wherein the weight ratio between the pridopidine and at least one of compounds 1-8 is in the range of 1:0.001 to 1:0.1. In other embodiments, the weight ratio between the pridopidine and at least one of compounds 1-8 is in the range of 1:0.005 to 1:0.1, In other embodiment, the weight ratio between the pridopidine and at least one of compounds 1-8 is in the range of 1:0.001 to 1:0.005.

In other embodiments, the concentration of compounds 1, 2, 3, 4, 5, 6, 7 or 8 or pharmaceutically acceptable salt thereof within the composition is between 0.001% w/w to 10% w/w. In other embodiments, the concentration of compounds 1, 2, 3, 4, 5, 6, 7 or 8 or pharmaceutically acceptable salt thereof within the composition is between 0.001% w/w to 0.05% w/w. In other embodiments, the concentration of compounds 1, 2, 3, 4, 5, 6, 7 or 8 or pharmaceutically acceptable salt thereof within the composition is between 0.001% w/w to 0.5% w/w. In other embodiments, the concentration of compounds 1, 2, 3, 4, 5, 6, 7or 8 or pharmaceutically acceptable salt thereof within the composition is between 0.001% w/w to 0.15% w/w. In other embodiments, the concentration of compounds 1, 2, 3, 4, 5, 6, 7 or 8 or pharmaceutically acceptable salt thereof within the composition is between 0.01% w/w to 0.15% w/w. In other embodiments, the concentration of compounds 1, 2, 3, 4, 5, 6, 7or 8 or pharmaceutically acceptable salt thereof within the composition is between 0.01% w/w to 0.5% w/w. In other embodiments, the concentration of compounds 1, 2, 3, 4, 5, 6, 7 or 8 or pharmaceutically acceptable salt thereof within the composition is between 0.01% w/w to 1% w/w.

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries. In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

In other embodiments, the composition described herein is administered orally, topically, intraocularly, intravitreally, periocularly or ocularly. In other embodiments, the composition described herein is administered by an eye drop application to the conjunctiva.

In other embodiments, the composition described herein is administered locally (e.g., in topical administration) or systemic (e.g., in enteral or parenteral administration).

"Local administration" as used herein refers to administration of the composition directly to where its action is desired, and specifically excludes systemic administration.

"Topical administration" as used herein refers to administration of the composition to body surfaces such as the skin or mucous membranes such as eyes.

"Ocular administration" as used herein refers to administration of the composition to the eye of a subject or to the skin around the eye (periocular skin) or the mucosa around the eye, specifically the conjunctiva of a subject, i.e., local administration. Examples of ocular administration include topical administration directly to the eye, topical application to the eye lid or injection into a portion of the eye or eye socket.

The composition described herein are administered orally, topically, intraocularly, intravitreally, periocularly, ocularly. In another embodiment, administered to the cornea, conjunctive, subconjunctival, subtenons, intracameral, intravitreal, subretinal, under the lid, retrobulbar.

In other embodiments, the composition described herein is administered by an eye drop application to the conjunctiva.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection.

The pharmaceutical composition for use in the methods of this invention is an oral dosage unit formulated as a tablet, a capsule, a pill, powder, liquid solution or as a liquid suspension.

In other embodiments, the composition described herein is formulated as eye drops, ophthalmic solutions, ophthalmic suspensions, ophthalmic emulsions, eye ointments, eye sprays.

In other embodiments, the pharmaceutical composition described herein may be in the form of an ophthalmic composition for topical application to an eye of a subject. The term "ophthalmic composition" as used herein will be understood to refer to any composition specifically formulated for direct and local administration to an eye of a patient. Said composition may be formulated for topical administration to the eye or for injection into the eye (i.e., intravitreal or intraocular injection). The ophthalmic composition may be provided in any formulation that allows for local administration thereof to the eye and allows the therapeutic compounds to function in accordance with the present disclosure. For example, but not by way of limitation, the ophthalmic composition may be provided in the form of a solution, drops, a mist/spray, plasters and pressure sensitive adhesives, an ointment, a lotion, a cream, a gel, lyophilized/spray-dried forms, and the like. In one particular non-limiting embodiment, the ophthalmic composition is provided in a form for topical application, such as but not limited to, an eyedrop formulation. In addition, the ophthalmic compositions of the present disclosure may be designed to provide delayed, controlled, extended, and/or sustained release using formulation techniques which are well known in the art.

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

General techniques and compositions for making dosage forms useful in the present inventio are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

"Treating" as used herein encompasses, e.g., inducing inhibition, regression, or stasis of a disease or disorder, e.g., glaucoma, or alleviating, lessening, suppressing, inhibiting, reducing the severity of, eliminating or substantially eliminating, or ameliorating a symptom of the disease or disorder. Treatment further comprises providing neuroprotection to an ocular cell, for example a retinal ganglion cell or optic nerve axon in a subject. The "neuroprotective" activity of pridopidine is disclosed herein. Neuroprotection comprises protection of neurons, for example RGC or optic nerve axon, from injury or death or b) improvement of neuronal function for example of RGC or optic nerve axon. As used herein, "neuroprotection" refers to reducing, preventing, attenuating and/or reversing progression of neurodegeneration. As used herein, "neurodegeneration" refers to the progressive loss of neurons, for example RGC or optic nerve axon loss, by injury or death. "Inhibition" of disease progression or disease complication in a subject means preventing or reducing the disease progression and/or disease complication in the subject.

A "symptom" associated with glaucoma includes any clinical or laboratory manifestation associated with glaucoma and is not limited to what the subject can feel or observe.

As used herein, a subject "afflicted" with glaucoma means the subject has been diagnosed with glaucoma.

As used herein, a subject at "baseline" is as subject prior to administration of pridopidine in a therapy as described herein.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "0.1 mg-40.0 mg" includes 0.1 mg, 0.2 mg, 0.3 mg, 0.4 mg, etc. up to 40.0 mg.

As used herein, a "fixed-dose combination" or "fixed-dosage combination" refers to a medicament which comprises two active agents. Typically, the two agents are very difficult to separate by means readily available to patients. Non-limiting examples include tablets, pills, or solutions comprising two agents.

In this application, when a comparative term is used, such as "the retinal ganglion cell (or optic nerve axon) loss is reduced by at least 10% in a subject" the comparison is relative to a subject afflicted with an analogous disease for example the control subject in a prior relevant clinical study, and not to a healthy subject. For example, the retinal ganglion cell (or optic nerve axon) loss may be compared to the average retinal ganglion cell (or optic nerve axon) loss in similarly diseased subjects without treatment with pridopidine. Thus, the comparison value may be obtained by reference to the placebo group of a clinical study.

The combination of the invention may be formulated for its simultaneous, separate or sequential administration, with at least a pharmaceutically acceptable earner, additive, adjuvant or vehicle as described herein. Thus, the combination of the two active compounds may be administered:

- as a combination that is part of the same medicament formulation, the two active compounds are then administered simultaneously, or
- as a combination of two units, each with one of the active substances giving rise to the possibility of simultaneous, sequential or separate administration.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine therapy to a glaucoma patient already receiving therapy with IOP reducing eye drops.

For the foregoing embodiments, each embodiment disclosed herein is contemplated as being applicable to each of the other disclosed embodiments. For instance, the elements recited in the method embodiments can be used in the pharmaceutical composition, package, and use embodiments described herein and vice versa.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Pridopidine Protects Retinal Ganglion Cells in the Rat Morrison Model of Glaucoma In order to test the efficacy of pridopidine for treating RGC degeneration and ultimate death, the well-established Morrison model for glaucoma was utilized. In this model, sclerosis of the aqueous veins via retrograde introduction of hypertonic saline increases intraocular pressure (IOP). Hypertonic saline injection (HSI) was performed on day 0 and day 7 into the episcleral veins of the right eye of pigmented Brown Norway. Rats were sedated with ketamine and xylazine (40-80 and 5-10 mg/kg, respectively), kept warm and eyes moist to avoid desiccation during the procedure. Eye surface was treated with erythromycin (0.5%). On Days 0 and 7, hypertonic saline solution (250 L, NaCl, 1.8-2.0M) was injected into the limbal vascular plexus via different episcleral veins in the OHT eye. For IOP measurement, corneas were anaesthetized with 0.5% proparacaine HCl ophthalmic solution and then IOP measured using a Tono-Pen Vet. Ten repeated readings were averaged from each eye. IOP and chronic ocular hypertension (OHT) induced neurodegeneration in the right eye (OD) similar to that in human patients with glaucoma, while the left eye served as control (OS).

Figure 1:
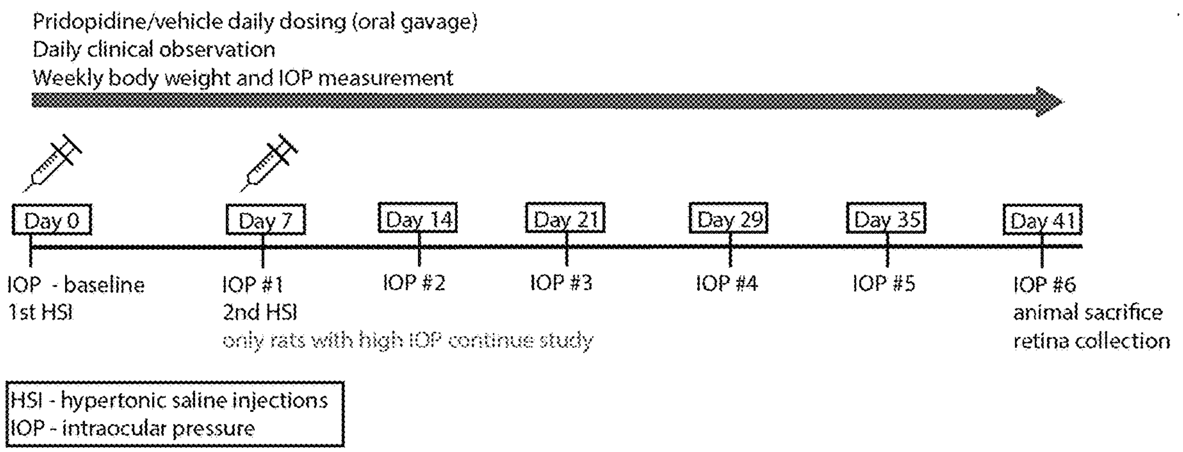
FIGS. 1-5: Pridopidine Rescues Retinal Ganglion Cells (RGCs) in the Morrison Model for Retinal Neurodegeneration.

Pridopidine at doses of 3, 30 and 60 mg/kg or control (double-distilled water, DDW) was administered daily by oral gavage, starting from day 1 after confirming IOP elevation until day 41. Over the course of the study, animals were clinically evaluated daily, and IOP and body weight measured weekly (FIG. 1). There was no significant change in body weight (Table 1, one-way ANOVA, P≥0.05 for all groups at any given time point).

TABLE 1

Summary of Body Weights-Morrison model

| | | | Day | | | | | | |
|---|---|---|---|---|---|---|---|---|---|
| Group | | | 0 | 7 | 14 | 21 | 28 | 35 | 41 |
| Pridopidine | DDW | Mean (g) | 243.35 | 248.5 | 246.48 | 247.23 | 257.93 | 249.18 | 250.05 |
| | | S.D. | 10.3 | 10.9 | 11.56 | 11.54 | 11.63 | 11.56 | 11.4 |
| | | N | 12 | 12 | 12 | 12 | 12 | 11 | 11 |
| | 3 mg/kg | Mean (g) | 244.58 | 250.96 | 248.35 | 249.97 | 250.34 | 251.39 | 251.83 |
| | | S.D. | 10.78 | 11.09 | 12.23 | 11 | 11.08 | 10.79 | 11.2 |
| | | N | 12 | 11 | 11 | 11 | 11 | 11 | 11 |
| | 30 mg/kg | Mean (g) | 246.52 | 252.05 | 249.25 | 249.97 | 250.63 | 251.59 | 252.09 |
| | | S.D. | 10.93 | 11.1 | 11.48 | 11.8 | 11.68 | 11.29 | 11.42 |
| | | N | 12 | 12 | 12 | 12 | 12 | 12 | 12 |

TABLE 1-continued

| Summary of Body Weights-Morrison model | | | | | | | | |
|---|---|---|---|---|---|---|---|---|
| | | Day | | | | | | |
| Group | | 0 | 7 | 14 | 21 | 28 | 35 | 41 |
| 60 mg/kg | Mean (g) | 245.84 | 251.66 | 249.71 | 250.75 | 252.73 | 253.68 | 254.1 |
| | S.D. | 10.91 | 11.2 | 11.59 | 11.06 | 10.85 | 10.52 | 10.96 |
| | N | 12 | 12 | 12 | 12 | 11 | 11 | 11 |

Figure 2:
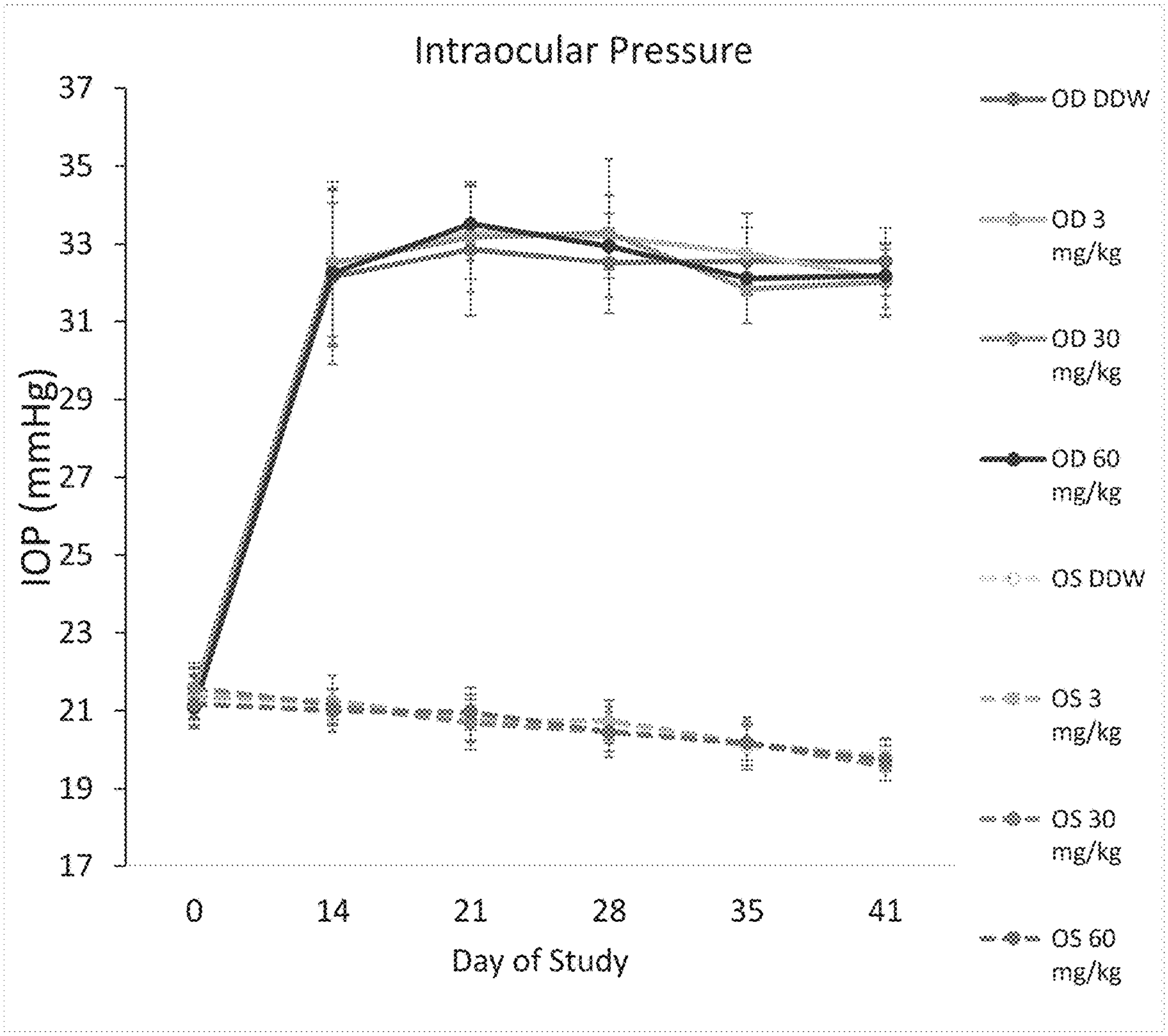

Baseline fop in both eyes ranged from 20.3 to 22.3 mml-lg in all animals before administration of the first dose. By Day 14, one week after the second hypertonic saline injection (HS), in the right eye (OD) the fop increased by 11.1±2.1 (mean±SD) mmHg from baseline of all treatment groups, compared to −0.3±0.6 mmHg in control left eyes (OS) (FIG. 2; Student's t-test, p≤0.0001). The elevation persisted until the end of the study (FIG. 2). Weekly assessment of lop can be seen in Table 2.

TABLE 2

| Weekly assessment of IOP in individual rats | | | | | | | |
|---|---|---|---|---|---|---|---|
| | | OD (injected right eye) | | | OS (control left eye) | | |
| Treatment Group | Rat number | IOP1-Day 0 (mmHg) | IOP1-Day 14 (mmHg) | ΔIOP (mmHg) | IOP1-Day 0 (mmHg) | IOP1-Day 14 (mmHg) | ΔIOP (mmHg) |
| DDW | 1001 | 22.4 | 30.6 | 8.2 | 21.9 | 20.7 | −1.2 |
| | 1002 | 21.5 | 30.3 | 8.8 | 22 | 21.6 | −0.4 |
| | 1003 | 22.2 | 29.4 | 7.2 | 21.5 | 20.7 | −0.8 |
| | 1004 | 21 | 30.3 | 9.3 | 22.3 | 21.4 | −0.9 |
| | 1005 | 20.3 | 30.6 | 10.3 | 21.2 | 21.7 | 0.5 |
| | 1006 | 20 | 32.6 | 12.6 | 20.7 | 20.7 | 0 |
| | 1007 | 21.7 | 35 | 13.3 | 21.8 | 21.7 | −0.1 |
| | 1008 | 21.8 | 35.4 | 13.6 | 22 | 21.7 | −0.3 |
| | 1009 | 21 | 29.6 | 8.6 | 20.5 | 20.8 | 0.3 |
| | 1010 | 20.6 | 34.4 | 13.8 | 21.2 | 20.8 | −0.4 |
| | 1011 | 22.7 | 33.3 | 10.6 | 21.8 | 21 | −0.8 |
| | 1012 | 21.4 | 34.2 | 12.8 | 20.6 | 20.7 | 0.1 |
| 3 mg/kg | 2001 | 21.8 | 29.4 | 7.6 | 21.4 | 21.9 | 0.5 |
| | 2002 | 20.8 | 29.7 | 8.9 | 20.6 | 20.8 | 0.2 |
| | 2003 | 21.3 | 30.2 | 8.9 | 20.3 | 20.9 | 0.6 |
| | 2004 | 20.8 | 30.4 | 9.6 | 21.3 | 20.8 | −0.5 |
| | 2005 | 21.7 | N/A | | 21.5 | N/A | |
| | 2006 | 20.8 | 32.5 | 11.7 | 22.2 | 20.9 | −1.3 |
| | 2007 | 21.4 | 34.1 | 12.7 | 20.9 | 20.3 | −0.6 |
| | 2008 | 21.2 | 34.8 | 13.6 | 21.4 | 22 | 0.6 |
| | 2009 | 20.1 | 33.5 | 13.4 | 21.3 | 21.5 | 0.2 |
| | 2010 | 20.9 | 33.8 | 12.9 | 21.9 | 21.1 | −0.8 |
| | 2011 | 21 | 34.4 | 13.4 | 21.1 | 21.2 | 0.1 |
| | 2012 | 21.2 | 34.4 | 13.2 | 22.2 | 22.5 | 0.3 |
| 30 mg/kg | 3001 | 21.7 | 30.4 | 8.7 | 21.7 | 21.4 | −0.3 |
| | 3002 | 20.9 | 31 | 10.1 | 21.5 | 21.4 | −0.1 |
| | 3003 | 21.2 | 30.1 | 8.9 | 22 | 20.8 | −1.2 |
| | 3004 | 22 | 30.3 | 8.3 | 21.2 | 20.8 | −0.4 |
| | 3005 | 20.6 | 34.9 | 14.3 | 21.6 | 21.3 | −0.3 |
| | 3006 | 22.4 | 34.2 | 11.8 | 21.2 | 21.2 | 0 |
| | 3007 | 21.3 | 30.4 | 9.1 | 21.7 | 21.7 | 0 |
| | 3008 | 22.7 | 33.3 | 10.6 | 22 | 21.2 | −0.8 |
| | 3009 | 20.6 | 33.7 | 13.1 | 21.4 | 20.8 | −0.6 |
| | 3010 | 21.1 | 34.8 | 13.7 | 21.2 | 20.7 | −0.5 |
| | 3011 | 21.4 | 33.2 | 11.8 | 21.9 | 20.7 | −1.2 |
| | 3012 | 21.6 | 33.9 | 12.3 | 21.5 | 21.8 | 0.3 |
| 60 mg/kg | 4001 | 20.7 | 30.6 | 9.9 | 21.3 | 21.4 | 0.1 |
| | 4002 | 21.4 | 30.4 | 9 | 21.4 | 21.3 | −0.1 |
| | 4003 | 21.4 | 30.7 | 9.3 | 20.8 | 21.1 | 0.3 |
| | 4004 | 21.7 | 30.6 | 8.9 | 21.2 | 21.9 | 0.7 |
| | 4005 | 21.3 | 33.9 | 12.6 | 21.6 | 21 | −0.6 |
| | 4006 | 21.4 | 34.9 | 13.5 | 21.2 | 21 | −0.2 |
| | 4007 | 21.4 | 30.8 | 9.4 | 20.5 | 20.7 | 0.2 |

TABLE 2-continued

| Weekly assessment of IOP in individual rats | | | | | | | |
|---|---|---|---|---|---|---|---|
| | | OD (injected right eye) | | | OS (control left eye) | | |
| Treatment Group | Rat number | IOP1-Day 0 (mmHg) | IOP1-Day 14 (mmHg) | ΔIOP (mmHg) | IOP1-Day 0 (mmHg) | IOP1-Day 14 (mmHg) | ΔIOP (mmHg) |
| | 4008 | 20.4 | 30.4 | 10 | 21.1 | 21.5 | 0.4 |
| | 4009 | 21.2 | 34.6 | 13.4 | 21.6 | 21 | −0.6 |
| | 4010 | 21.2 | 33.9 | 12.7 | 20.6 | 20.4 | −0.2 |
| | 4011 | 20.4 | 33.2 | 12.8 | 21.2 | 19.8 | −1.4 |
| | 4012 | 20.4 | 32.9 | 12.5 | 21.6 | 20.9 | −0.7 |

Eligibility of animals for RGC analysis at the end of the study was determined by averaging the ΔIOP ($\Delta IOP = IOP_{OD} - IOP_{OS}$) at four weekly timepoints (Days 21, 29, 35 and 41). Mean ΔIOP in all animals ranged from 11.5 to 13.4 mmHg (Table 3). Pridopidine at all doses has no effect on IOP in either the test or control eye (FIG. 2).

TABLE 3

| Δ IOP in Morrison model rats | | | | | | | |
|---|---|---|---|---|---|---|---|
| Treatment | Subject Name | Δ IOP3 mmHg (Day21) | Δ IOP4 mmHg (Day 29) | Δ IOP5 mmHg (Day35) | Δ IOP6 mmHg (Day41) | Average ΔIOP (3-6) mmHg | Eligible for Immunostaining |
| DDW | 1001 | 11.0 | 13.1 | 12.1 | 13.2 | 12.4 | yes |
| | 1002 | 15.3 | 10.4 | 13.2 | 12.3 | 12.8 | yes |
| | 1003 | 12.7 | 12.2 | 12.4 | 13.3 | 12.7 | yes |
| | 1004 | 11.6 | 10.9 | 12.1 | 12.9 | 11.9 | yes |
| | 1005 | 12.8 | 10.5 | 11.7 | 12.5 | 11.9 | yes |
| | 1006 | 8.6 | N/A | N/A | N/A | N/A | N/A |
| | 1007 | 12.3 | 11.4 | 13.7 | 11.5 | 12.2 | yes |
| | 1008 | 12.8 | 12.3 | 13.1 | 11.8 | 12.5 | yes |
| | 1009 | 9.6 | 11.3 | 13.0 | 13.6 | 11.9 | yes |
| | 1010 | 10.7 | 12.3 | 13.4 | 13.2 | 12.4 | yes |
| | 1011 | 14.5 | 13.4 | 12.0 | 12.6 | 13.1 | yes |
| | 1012 | 12.9 | 10.9 | 10.6 | 12.4 | 11.7 | yes |
| Pridopidine 3 mg/kg | 2001 | 12.8 | 13.4 | 12.2 | 11.8 | 12.6 | yes |
| | 2002 | 11.8 | 12.7 | 12.7 | 12.3 | 12.4 | yes |
| | 2003 | 12.9 | 15.6 | 14.0 | 11.1 | 13.4 | yes |
| | 2004 | 13.7 | 11.1 | 10.7 | 13.8 | 12.3 | yes |
| | 2005 | N/A | N/A | N/A | N/A | N/A | N/A |
| | 2006 | 12.4 | 12.0 | 12.7 | 12.0 | 12.3 | yes |
| | 2007 | 10.7 | 13.6 | 12.3 | 10.2 | 11.7 | yes |
| | 2008 | 12.8 | 9.5 | 12.7 | 12.6 | 11.9 | yes |
| | 2009 | 11.2 | 12.1 | 12.9 | 12.6 | 12.2 | yes |
| | 2010 | 14.1 | 12.7 | 11.2 | 13.4 | 12.9 | yes |
| | 2011 | 12.8 | 13.4 | 13.3 | 12.7 | 13.1 | yes |
| | 2012 | 13.0 | 10.8 | 13.9 | 12.4 | 12.5 | yes |
| Pridopidine 30 mg/kg | 3001 | 12.6 | 12.5 | 12.8 | 12.2 | 12.5 | yes |
| | 3002 | 13.1 | 11.8 | 10.0 | 13.5 | 12.1 | yes |
| | 3003 | 13.5 | 13.5 | 11.5 | 11.1 | 12.4 | yes |
| | 3004 | 11.9 | 13.6 | 12.5 | 13.0 | 12.8 | yes |
| | 3005 | 13.0 | 13.1 | 10.1 | 12.3 | 12.1 | yes |
| | 3006 | 9.5 | 13.6 | 12.7 | 12.5 | 12.1 | yes |
| | 3007 | 13.6 | 12.4 | 11.5 | 12.6 | 12.5 | yes |
| | 3008 | 12.4 | 12.5 | 12.3 | 12.2 | 12.4 | yes |
| | 3009 | 14.5 | 13.1 | 12.0 | 12.2 | 13.0 | yes |
| | 3010 | 10.9 | 11.2 | 10.8 | 14.0 | 11.7 | yes |
| | 3011 | 11.1 | 15.1 | 12.1 | 10.9 | 12.3 | yes |
| | 3012 | 13.8 | 11.6 | 11.7 | 12.6 | 12.4 | yes |
| Pridopidine 60 mg/kg | 4001 | N/A | N/A | N/A | N/A | N/A | N/A |
| | 4002 | 13.6 | 13.5 | 12.2 | 12.8 | 13.0 | yes |
| | 4003 | 13.0 | 12.9 | 12.5 | 12.9 | 12.8 | yes |
| | 4004 | 11.8 | 13.1 | 11.6 | 13.0 | 12.4 | yes |
| | 4005 | 11.0 | 12.5 | 11.9 | 10.5 | 11.5 | yes |
| | 4006 | 11.3 | 11.9 | 11.8 | 13.2 | 12.1 | yes |
| | 4007 | 13.7 | 13.0 | 11.7 | 12.8 | 12.8 | yes |
| | 4008 | 12.6 | 11.7 | 11.8 | 12.0 | 12.0 | yes |
| | 4009 | 12.6 | 11.9 | 11.7 | 12.1 | 12.1 | yes |
| | 4010 | 12.2 | 12.1 | 11.7 | 12.3 | 12.1 | yes |
| | 4011 | 14.3 | 12.5 | 11.3 | 13.1 | 12.8 | yes |
| | 4012 | 12.1 | 12.3 | 13.1 | 12.2 | 12.4 | yes |

Figure 3:
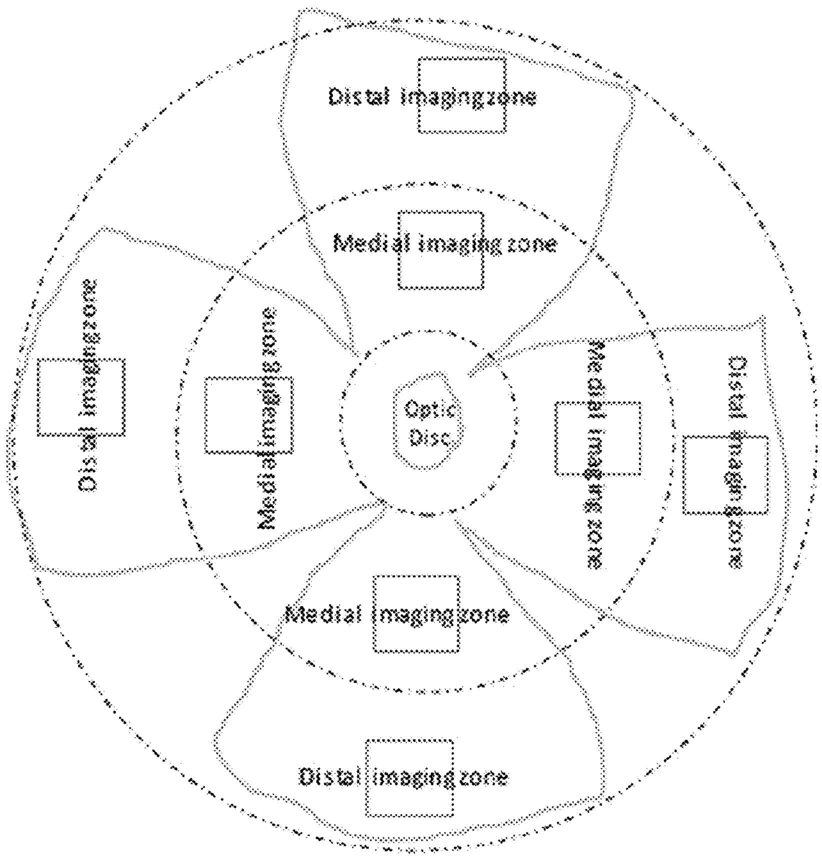

The number of RGCs was quantified using immunofluorescent staining for the RGC marker brain-specific homeobox/POU domain protein 3A. (Brn-3a), followed by image analysis. Eyes were immediately enucleated following $CO_2$ euthanization and fixed in paraformaldehyde (PFA, 4%) at 4° C. for 24 hours, then dissected in PBS. Retinas were permeabilized in PBS+0.5% Triton X-100 for 15 minutes, frozen at −80° C. for 15 minutes, then rinsed in PBS-0.5% Triton. Samples were incubated overnight at 4° C. with anti-Brn-3a primary antibody (Brn-3a 14A6 #sc-8429) in blocking solution (PBS, 2% normal donkey serum, 2% Triton X-100). Retinas were washed 3× in PBS and incubated with fluorescent secondary antibodies (anti-mouse IgG (H+L), Alexa Fluor 594, #A21203) in blocking buffer, then washed 3 times. Four radial cuts were made in the retina and it was flat-mounted. Two regions of interest (medial and distal) were acquired in each quadrant (FIG. 3) with fluorescent microscopy, and RGCs counted using ImageJ.

Figure 4:
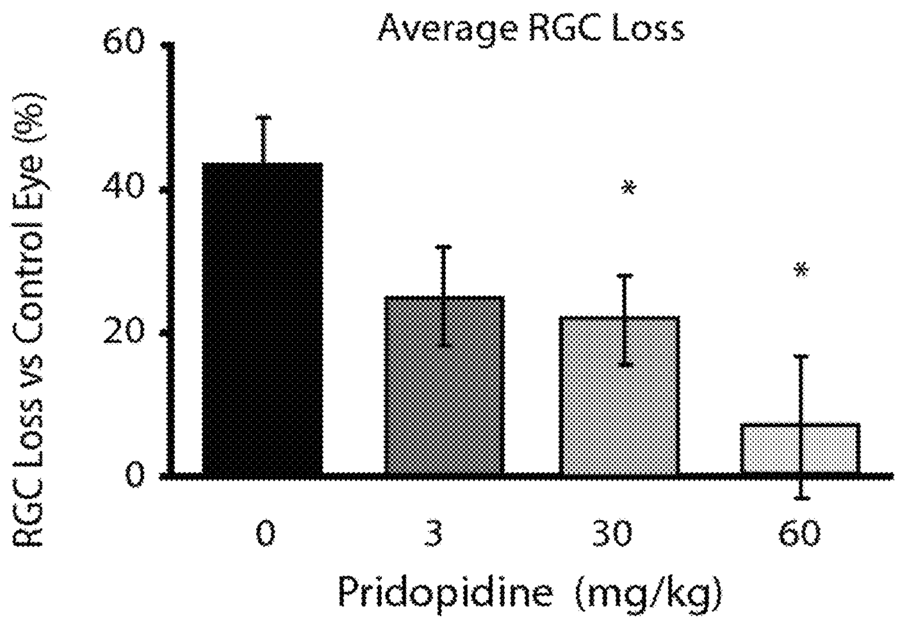
Figure 5:
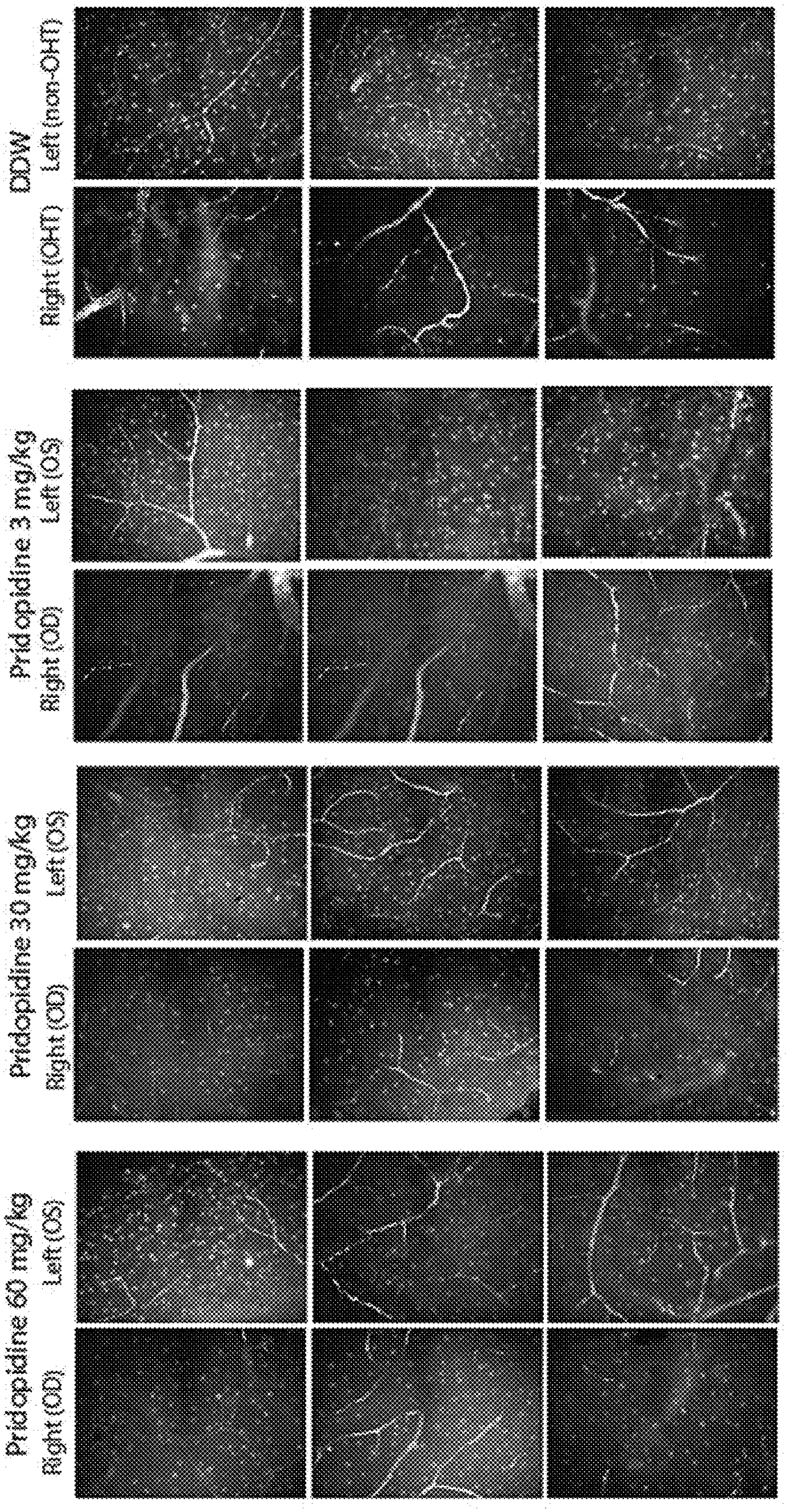

IOP and the ensuing chronic ocular hypertension (OHT) induced neurodegeneration in the right eye (OD) similar to that in human patients with glaucoma, while the healthy left eye (OS) served as control. The percent of RGC loss was calculated by comparing the number of RGC counts per retina in the OD eye to that in the OS eye from the same animal. Pridopidine shows significant protection of RGCs. RGC Loss (%) (mean±SEM), was 43±6% in the control group, 25±7% in the pridopidine 3 mg/kg (p=0.068), 21±6% in the pridopidine 30 mg/kg (p=0.019), and 7±9% in the pridopidine 60 mg/kg (p=0.005) (FIG. 4). RGC neuroprotection (%) in each animal was calculated as following: [100×((1−RGC Loss (%)/Average RGC Loss (%) in Control group))]. Compared to vehicle control, pridopidine treatment results in RGC neuroprotection of 50% (p=0.019) and 83% (p=0.005) with the 30 and 60 mg/kg doses, respectively. Representative images of RGC staining can be seen in FIG. 5.

The results of the Morrison rat model are surprising and unexpected: in comparison to the RGC loss in control animals treated with double-distilled water (DDW), pridopidine doses of 30 and 60 mg/kg demonstrate robust and significant protection of RGC loss of 50% (p=0.019) and 83% (p=0.005). Lower dose of 3 mg/kg shows a positive trend of 42% protection, (p=0.068).

Example 2: Pridopidine Binds Strongly to Melanin

To evaluate pridopidine binding to melanin, the retention of $^{14}C$-pridopidine in different tissues in the rat was evaluated. A single 3 mg free base/1 mL/kg dose of $^{14}C$-pridopidine was administered to male Long Evans brown rats and radioactivity assessed over time in pigmented and non-pigmented tissues. The rats were fasted from 16 hours before to 4 hours after administration. Animals were sacrificed by exsanguination from the abdominal vena cava under ether anesthesia.

At 24 hours post-administration, a whole-body autoradiogram was prepared. Hair was clipped, the nasal cavity and anus filled with 4% carboxymethyl cellulose sodium (CMC-Na), and the carcass frozen in a dry ice-acetone mixture. After removal of extremities, carcass was embedded in 4% CMC-Na, frozen again in dry ice-acetone, sectioned in a cryomicrotome (30 μm) and collected onto adhesive tape. Sections were lyophilized for 3 days, then covered with a protective membrane and placed in contact with an imaging plate for one day exposure in a sealed lead box. Radioactivity was analyzed using BAS2500.

Quantification of radioactivity in tissues was performed at designated time points. Blood was collected from the abdominal vena cava. Plasma was separated from the remaining blood. Tissues were collected and solubilized with 2 mL of Soluene-350 with heating. Samples were mixed with 10 mL of the scintillator Hionic-Fluor, and radioactivity measured using LSC (Liquid Scintillation Counter). Radioactivity in blood cells was calculated using the radioactivity concentrations in blood and plasma.

Radioactivity (dpm) was counted using LSC for 2 min after scintillator addition. Counting efficiency was corrected by the external standard source method. Detection limit was defined as 2× background value.

At 24 hours after administration, whole-body radioluminograms demonstrate a high level of radioactivity in melanin-containing uveal tissues (FIG. 6), while lower levels of radioactivity were detected in other tissues tested, including the skin and spleen. The magnified radioluminogram of the eye confirms the high level of radioactivity in the uveal tract (FIG. 7) and shows that pridopidine has a strong binding affinity for melanin.

Quantification of radioactivity demonstrates increasing pridopidine binding in the eye after administration, reaching a maximal level at 168 hours (1 week). Only at 672 hours (4 weeks) after administration did the radioactivity concentration in the eye decrease, to 7% of its maximum. In contrast, other tissues (with the exception of pigmented skin) reach maximal pridopidine binding 1 hour after administration. At 24 hours after administration binding decreases to 3% or less of maximum, and at 72 hours after administration decreases to 2% or less of the maximum (FIG. 8).

These data confirm that pridopidine is retained in pigmented tissue, potentially binding strongly to melanin.

Example 3: Pridopidine Protects Retinal Ganglion Axons in Albino Wistar Rats

To test whether pridopidine binding to melanin affects its neuroprotective activity, the effect of pridopidine on retinal ganglion cell and axon loss was evaluated in glaucomatous Wistar rats, which are albino and do not synthesize melanin.

In Wistar rats, the laser coagulation (LC) model of experimental glaucoma was utilized.

Figure 9:
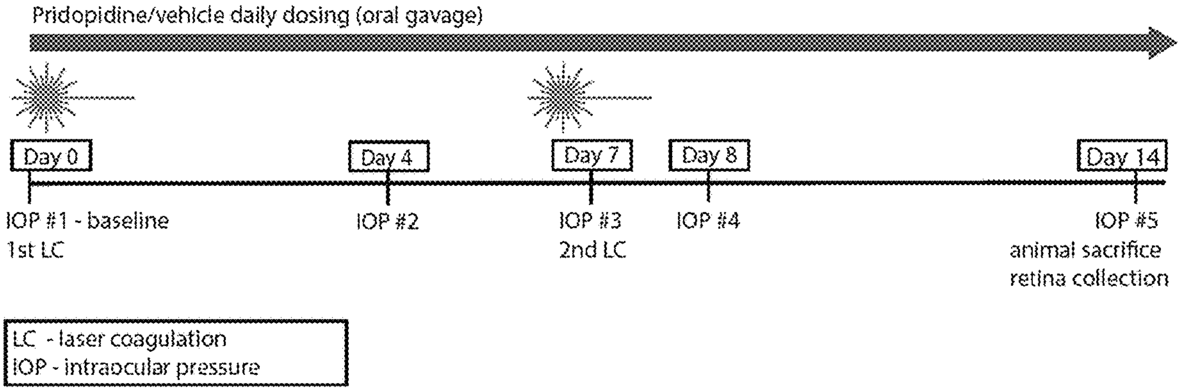

Unilateral induction of IOP elevation was performed twice, at day 0 and day 7. IOP increase was induced by 532 nm diode laser (Oculight® TX; Iridex) photocoagulation of episcleral veins, as previously described. IOP was measured with a TonoLab tonometer. All lasered eyes had IOP of 18 mmHg or higher as assessed on day 1 (FIG. 9).

Pridopidine at doses of 3, 30 and 60 mg/kg or vehicle control was administered by oral gavage daily, starting from day 1, after confirming IOP elevation. IOP was measured at baseline, and after laser photocoagulation on days 1, 4, 7, 8, and 14 (FIG. 10).

Baseline IOP of both eyes ranged from 9.6 to 16 mmHg in all animals pre-treatment. Laser photocoagulation of the episcleral veins significantly increases IOP by 20.4±7.4 mmHg from baseline in all treatment groups, compared to a change in control left eyes of 1.2±2.3 mmHg from baseline (FIG. 10 and Table 4; Student's t-test, P≤0.0001). The peak elevation was within a day of laser photocoagulation and returned to baseline 7 days later. There was no difference in the IOP of lasered eyes based on the treatment administered (FIG. 10; one-way ANOVA, followed by Dunn's multiple comparisons test, P≥0.26 for all groups).

TABLE 4

| Area under curve (AUC) of IOP in different treatment groups and in contralateral eyes of vehicle-treated animals (reference). | | | | | |
|---|---|---|---|---|---|
| | | | Pridopidine | | |
| | Control | Vehicle | 3 mg/kg | 30 mg/kg | 60 mg/kg |
| Total Area | 185 | 272 | 255 | 289 | 295 |
| Std. Error | 8.3 | 46 | 35 | 69 | 62 |

With respect to animal weight, there were no statistically significant differences between the groups at any time point analyzed (Table 5; one-way ANOVA, P≥0.25 for all groups at any given time point).

TABLE 5

| Summary of body weights - LC model | | | | | |
|---|---|---|---|---|---|
| | | | Pridopidine | | |
| Day | | Vehicle | 3 mg/kg | 30 mg/kg | 60 mg/kg |
| 0 | Mean (g) | 520 | 539 | 527 | 535 |
| | STDEV | 39 | 41 | 36 | 28 |
| 7 | Mean (g) | 543 | 551 | 539 | 537 |
| | STDEV | 39 | 41 | 33 | 26 |
| 14 | Mean (g) | 546 | 559 | 538 | 536 |
| | STDEV | 41 | 40 | 34 | 27 |

On day 14, rats were sacrificed by transcardial perfusion, first with 0.9% NaCl solution, then with 4% PFA in 0.1M phosphate buffer, pH7.4. Eyes and optic nerves were collected for immunohistochemical analysis. The number of RGCs was quantified using immunofluorescent staining for RNA-binding protein with multiple splicing (RBPMS), an RGC-specific marker, and DAPI nuclear stain followed by stereological analysis of the entire retina (FIG. 11).

Because of the variability in IOP associated with the laser photocoagulation model, including high IOPs immediately after onset which could be associated with retinal ischemia or low IOP's which could indicate failure to establish the model, an inclusion criterion of initial IOP<45 mml-Ig, and all animals with a cumulative IOP of >125 mmHg was applied, as long as no individual IOP measurement exceeded 55 mmHg at any time point. In addition, the IOP in the injected eye compared to the contralateral left eye had to be elevated by at least 6 mmHg after the second injection, and at no time greater than 55 mmHg. The number of RGCs per retinal area after application of these criteria can be seen in Table 6.

TABLE 6

| The number of RGCs per retinal area of lasered eyes in different treatment groups | | | | | |
|---|---|---|---|---|---|
| | | | Pridopidine | | |
| Eye | | Vehicle | 3 mg/kg | 30 mg/kg | 60 mg/kg |
| Control | Mean | 1508 | 1404 | 1444 | 1417 |
| | STDEV | 223 | 226 | 87 | 296 |
| Lasered | Mean | 1280 | 1315 | 1336 | 1198 |
| | STDEV | 234 | 112 | 178 | 295 |
| Difference | % | 16.7 | 5.2 | 7.7 | 13.9 |

In all groups, the number of RGCs in lasered eyes is significantly decreased compared to contralateral left control eyes (paired-samples t-test or Wilcoxon test P≤0.047 for all). In the vehicle-treated group, RBPMS-positive RGCs in the right eye decrease by 16.7% compared to the control left eye. A trend towards neuroprotection is demonstrated for the 3 mg/kg and 30 mg/kg doses, at which cell numbers in the right eye decrease by 5.2% and 7.7% compared to the control left eyes, respectively. In the 60 mg/kg group RGCs decrease by 13.9% compared to control eye (FIG. 12).

Example 4: Pridopidine Protects Optic Nerve Axons in Albino Wistar Rats

Neuroprotective preservation of visual function in glaucoma and other optic neuropathies depends not only on preservation of cell bodies, but also on maintaining connectivity between the eye and the brain. Connectivity is preserved by protecting RGC axons which make up the optic nerve. Axon loss was evaluated in albino Wistar rats using the laser coagulation model as in Example 3. Unilateral induction of IOP elevation was performed twice, at day 0 and day 7. IOP increase was induced by 532 nm diode laser (Oculight® TX; Iridex) photocoagulation of episcleral veins, as previously described. IOP was measured with a TonoLab tonometer. All lasered eyes had IOP of 18 mmHg or higher as assessed on day 1.

Pridopidine at doses of 3, 30 and 60 mg/kg or vehicle control was administered by oral gavage daily, starting from day 1, after confirming IOP elevation IOP was measured at baseline, and after laser photocoagulation on days 1, 4, 7, 8, and 14.

On day 14, rats were sacrificed by transcardial perfusion, first with 0.9% NaCl solution, then with 4% PFA in 0.1M phosphate buffer, pH 7.4. Eyes and optic nerves were collected for immunohistochemical analysis.

Optic nerves were postfixed in 4% PFA (in 0.1M phosphate buffer, pH 7.4), placed in 1% osmium, dehydrated in ascending alcohol concentrations, and placed in 1% uranyl acetate in 100% ethanol for 1 hour. Optic nerves were embedded in epoxy resin mixture at 60° C. for 48 hours and 1 μm sections prepared. Axon number was estimated using stereology.

High IOPs immediately after LC procedure could be associated with retinal ischemia, and low IOP's could indicate failure to establish the model. Therfore, an inclusion criterion of initial IOP<45 mmHg, and all animals with a cumulative IOP of >125 mmHg was applied, as long as no individual IOP measurement exceeded 55 mmHg at any time point. In addition, the IOP in the injected eye compared to the contralateral left eye had to be elevated by at least 6 mmHg after the second injection, and at no time greater than 55 mmHg. The mean number of axons in treated and untreated eyes per group after applying this criterion are summarized in Table 7.

TABLE 7

Number of optic nerve axons in contralateral control eyes and in the laser-treated eyes after 125/55 inclusion criterion was applied

| Eye | | Vehicle | Pridopidine 3 mg/kg | Pridopidine 30 mg/kg | Pridopidine 60 mg/kg |
|---|---|---|---|---|---|
| Control | Mean | 444 | 394 | 433 | 395 |
| | STDEV | 58.3 | 28.5 | 62 | 36.3 |
| Lasered | Mean | 323 | 358 | 363 | 365 |
| | STDEV | 46 | 28 | 29 | 29 |
| Difference | % | 16.7 | 8.6 | 15 | 7.6 |

The greatest loss of optic nerve axons is observed in vehicle animals (27.5% from control eye). Pridopidine 3 mg/kg, the lowest dose tested, demonstrates a significant protection of axon loss (only 8.6% loss of optic nerve axons vs. control eye, p=0.006). Higher doses of pridopidine, 30 mg/kg and 60 mg/kg, similarly demonstrate a significant protective effect on optic nerve axons (15%, p=0.04 and 7.24%, p=0.002, respectively, 1-way ANOVA test followed by Dunnett's post-hoc test) (FIG. 13 and FIG. 14). Axonal protection (%) in each animal was calculated as following: [100×((1−axon Loss (%)/Average axon loss (%) in Control group))]. Compared to the vehicle group, pridopidine demonstrates protection of RGC axons in optic nerves of 69%, 45% and 74% at the 3, 30 and 60 mg/kg doses, respectively.

Example 5: Topical Administration of Pridopidine

The Rat Glaucoma Model of Example 1 is performed as described above with the exception that pridopidine is topically administered to the HSI treated eye of the rats of groups 2, 3, and 4 instead of orally administered. The amount of pridopidine administered to rats in group 4 is greater than the amount of pridopidine administered in group 3 and the amount of pridopidine administered to rats in group 3 is greater than the amount of pridopidine administered to rats in group 2. Similar to Example 1, no pridopidine is administered to rats in group 1. Pridopidine significantly increases viability of the RGCs and reduces RCG loss in groups 2, 3 and 4 compared to group 1. Additionally, pridopidine protects RGC axons.

Example 6: Combination Therapy

The Rat Glaucoma Model of Example 1 is performed as described above with the exception that in addition to oral pridopidine, rats in each of Groups 1, 2, 3 and 4 are also treated with IOP reducing eye drops daily approximately between 8 a.m. and 10 a.m., starting on the day of the first HSI until euthanasia, which is the last day of dosing. This periodic administration of pridopidine in combination with IOP reducing eye drops to rats in this model provides increased efficacy (provides at least an additive effect or more than an additive effect) in treating the rats than when pridopidine is administered alone or when the IPO reducing eye drops are administered alone (at the same dose). The combination therapy also provides efficacy (provides at least an additive effect or more than an additive effect) in treating the rats without undue adverse side effects or affecting the safety of the treatment.

The combination therapy provides a clinically meaningful advantage and is more effective (provides at least an additive effect or more than an additive effect) in treating the patient than when pridopidine or IOP reducing eye drops are administered alone (at the same dose) in the following manner:

1. The combination therapy is more effective (provides an additive effect or more than an additive effect) in increasing viability of the RGCs in groups 2, 3 and 4 compared to group 1.
2. The combination therapy is more effective (provides an additive effect or more than an additive effect) in reducing RCG loss in groups 2, 3 and 4 compared to group 1.

Example 7: Assessment of Efficacy of Pridopidine for Treating Patients Afflicted with Glaucoma Long-term (e.g., daily or twice daily, or less than daily) administration of pridopidine (oral) is effective in treating human patients with glaucoma. Long-term (e.g., daily or twice daily, or less than daily) administration of pridopidine is effective to reduce a glaucoma-associated symptom in the subject.

A pridopidine composition as described herein is administered systemically to a subject or topically to the eye to of a subject suffering from glaucoma. The administration of the composition is effective to treat the subject suffering from glaucoma. The administration of the composition is also effective to reduce a glaucoma-associated symptom of glaucoma in the subject. The administration of the composition is effective to reduce RGC damage and/or RGC loss, and prevents (partly) a further shrinking of the visual filed in the subject.

Example 8: Assessment of Efficacy of Pridopidine for Treating Patients Afflicted with Dry Age-Related Macular Degeneration (AMD)

Long-term (e.g., daily or twice daily, or less than daily) administration of pridopidine (oral) is effective in treating human patients with dry AMD. Long-term (e.g., daily or twice daily, or less than daily) administration of pridopidine is effective to reduce a dry AMD-associated symptom in the subject, for example visual acuity. The decline of visual acuity that finally leads to functional blindness of the patients is attenuated or stopped. In some patients, visual acuity is partly restored. The pathological correlation for the decline of visual acuity is the progressive expansion of the degenerated area of the retina (i.e., geographic atrophy), specifically in the macula. The significantly reduced progression of the degenerative area is monitored with, for example, a computer-assisted fluorescence technique.

A pridopidine composition as described herein is administered systemically to a subject or topically to the eye of a subject suffering from dry AMD. The administration of the composition is effective to treat the subject suffering from dry AMD. The administration of the composition is also effective to reduce a dry AMD-associated symptom of dry AMD in the subject and to avoid progression of the dry form of AMD to the late stage wet form.

Example 9: Assessment of Efficacy of Pridopidine for Treating Patients Afflicted with Wet Age-Related Macular Degeneration (AMD)

Long-term (e.g., daily or twice daily) administration of pridopidine (oral) is effective in treating human patients with wet AMD. Long-term (e.g., daily or twice daily) administration of pridopidine is effective to reduce wet AMD-associated symptoms in the subject and improve eye-sight.

A pridopidine composition as described herein is administered systemically to a subject or topically to the eye of a subject suffering from wet AMD. The administration of the composition is effective to treat the subject suffering from wet AMD. The administration of the composition is also effective to reduce a wet AMD-associated symptom of wet AMD in the subject.

Example 10: Assessment of Efficacy of Pridopidine for Treating Patients Afflicted with Retinitis Pigmentosa Periodic (e.g., daily or twice daily or less than daily) administration of pridopidine (oral) is effective in treating human patients with retinitis pigmentosa. Periodic (e.g., daily or twice daily or less than daily) administration of pridopidine is effective to reduce a retinitis pigmentosa-associated symptom in the subject.

A pridopidine composition as described herein is administered systemically to a subject or topically to the eye of a subject suffering from retinitis pigmentosa. The administration of the composition is effective to treat the subject suffering from retinitis pigmentosa. The administration of the composition is also effective to reduce a retinitis pigmentosa-associated symptom of retinitis pigmentosa in the subject.

Example 11: Assessment of Efficacy of Pridopidine for Treating Patients Afflicted with Optic Neuropathy Long-term (e.g., daily or twice daily or less than daily) administration of pridopidine (oral) is effective in treating human patients with optic neuropathy. Long-term (e.g., daily or twice daily or less than daily) administration of pridopidine is effective to reduce an optic neuropathy-associated symptom in the subject.

A pridopidine composition as described herein is administered systemically to a subject or topically to the eye of a subject suffering from optic neuropathy. The administration of the composition is effective to treat the subject suffering from optic neuropathy. The administration of the composition is also effective to reduce an optic neuropathy-associated symptom of optic neuropathy in the subject.

Treatment of a subject afflicted with Leber's hereditary optic neuropathy with pridopidine in the manner of this example results in an analogous outcome.

In any of the examples listed above, pridopidine may be administered locally, i.e. by eye drops directly to the eye, and analogous results are obtained.

Example 12: Synergistic Effect of Pridopidine and Compound 1 or Pridopidine and Compound 4

Compound 1 and Compound 4 both display a synergistic effect with pridopidine on BDNF secretion from B104 neuroblastoma cells.

Compound 1 and Compound 4 show selective binding to the Sigma-1 Receptor (SIR, Ki=0.37 μM for compound 1 and Ki=2.9 μM for compound 4) with no binding to the Sigma-2 receptor (S2R. Ki>100 μM for both compound 1 and 4), as shown in Table 8.

TABLE 8

Binding affinity of pridopidine, Compound 1 and Compound 4 to the Sigma-1 and Sigma-2 receptors

| Compound | S1R Ki (μM) | S2R Ki (μM) | S1R fold selectivity (S2R/S1R) |
|---|---|---|---|
| Pridopidine | 0.057 | 5.45 | 96 |
| Compound 1 | 0.37 | >100 | >270 |
| Compound 4 | 2.9 | >100 | >35 |

In-vitro binding assays performed at Eurofins Pan/abs Taiwan, Ltd. Specific ligand binding was determined in the presence of an excess of unlabelled ligand Inhibition constants (Ki) were calculated from in vitro binding assays using the Cheng Prusoff equation (Cheng and Prusoff 1973). Source: Johnston et al, 2019 (Johnston et al. 2019) and NC20-PHARM-2.

Thus, both Compound 1 and Compound 4 have high affinity to the S1R and no affinity (Ki>100) to the S2R.

Reductions in Brain-Derived Neurotrophic Factor (BDNT) levels play a key role in the pathogenesis of neurodegenerative disorders and its levels are reduced in neurodegenerative and neurodevelopmental disorders such as Huntington disease (HD), Parkinson's disease, Alzheimer's disease (Zuccato and Cattaneo 2009) and Rett syndrome (Katz 2014).

Pridopidine demonstrates a dose dependent increase in BDNF secretion in rat neuroblastoma cells using an in-situ ELISA assay. This effect is mediated by activation of SIR, since pharmacological inhibition of the SIR abolished pridopidine's effect (Geva, et al. 2016).

When assessing the effect of Compound 1 or Compound 4 with pridopidine, the applicant identified an unexpected synergistic effect. The effect was observed in a BDNF in-situ ELISA assay (Geva, et al. 2016).

Thus, the synergistic effect on BDNF release demonstrated below is directly relevant to the therapeutic effect of pridopidine and compound 1 and compound 4.

The following data surprisingly and unexpectedly show that pridopidine together with either Compound 4 or Compound 1 demonstrates a synergistic effect on BDNF release.

Synergistic Effect of Compound 4 and Pridopidine on BDNF Release.

Pridopidine alone induces an increase in BDNF release of +13.6% at a concentration of 0.001 μM and +26% at a concentration of 0.005 μM, compared to control untreated cells. Compound 4 at a concentration of 0.001 μM alone has no effect on BDNF release compared to untreated control cells (−1.5%) However, pridopidine and Compound 4 together have an unexpected synergistic effect on BDNF release.

Pridopidine 0.001 μM+Compound 4 at 0.001 μM induce a 59.1% increase in BDNF release compared to control untreated cells (FIG. 15A).

Pridopidine 0.005 μM+Compound 4 at 0.001 μM induce an 80.7% increase in BDNF release compared to control untreated cells (FIG. 15B).

The effect of pridopidine and Compound 4 together is greater than the sum of the effects of each compound individually, indicating a surprising synergistic effect on BDNF secretion. The results are shown where the values are presented as percent (%) of change compared to untreated control.

Synergistic Effect of Compound 1 and Pridopidine on BDNF Release

Pridopidine alone at a concentration of 0.01 μM induces an increase in BDNF release compared to control untreated cells of +3.4%. Compound 1 alone at a concentration of 1 μM induces a +12.5% increase in BDNF release compared to control. However, pridopidine and Compound 1 together have a synergistic effect on BDNF release (+53.1%).

Pridopidine (0.01 μM)+Compound 1 (1 μM) induce a 53.1% increase in BDNF release compared to control untreated cells (FIG. 16).

Again, these results indicate a surprising and unexpected synergistic effect of pridopidine and Compound 1 on BDNF secretion as their effect when administered together (+53.1%) is greater than the sum of the effects of each compound individually.

Thus, the applicant has shown that Compounds 1 and Compound 4 have selective binding affinity to the S1R, together with a surprising and unexpected synergistic effect with pridopidine on BDNF release.

CONCLUSIONS

We studied the potential therapeutic effects of pridopidine in two different experimental glaucoma models in which retinal degeneration is induced by elevated IOP. Pridopidine demonstrates a neuroprotective effect on RGCs in both models. Surprisingly, pridopidine's protective effect is not mediated by lowering IOP, suggesting therapeutic potential for optic neuropathies beyond glaucoma.

REFERENCES

"Glaucoma", Merck Manual of Diagnosis and Therapy (1999), Merck Research Laboratories, (Whitehouse Station, Nt), 733-738.

Alward, "Medical Management of Glaucoma", N Eng J Med, 1998; 339:1298-1307).

Coleman "Glaucoma", Lancet, 1999; 354:1803-1810.

CSID:25948790, www.chemspider.com/Chemical-Structure.25948790.html (accessed 23:27, Jul. 15, 2016).

CSID:7971505, www.chemspider.com/Chemical-Structure.7971505.html (accessed 23:33, Jul. 15, 2016).

Eddings, Chelsy R., Nicolas Arbez, Sergey Akimov, Michal Geva, Michael R. Hayden, and Christopher A. Ross. 2019. "Pridopidine Protects Neurons from Mutant-Huntingtin Toxicity via the Sigma-1 Receptor." *Neurobiology of Disease*. https://doi.org/10.1016/j.nbd.2019.05.009.

Farkas et al., "Apoptosis, Neuroprotection and Retinal Ganglion Cell Death: An Overview", Int Ophthalmol Clin 2001; 41:111-13 0.

Geva, Michal, et al. 2016. "Pridopidine Activates Neuroprotective Pathways Impaired in Huntington Disease." *Human Molecular Genetics* 25 (18): 3975-87. https://doi.org/10.1093/hmg/ddw238.

Ionescu, Ariel, et al. 2019. "Targeting the Sigma-1 Receptor via Pridopidine Ameliorates Central Features of ALS Pathology in a SOD1G93A Model." *Cell Death & Disease* 10 (3). 210. https://doi.org/10.1038/s41419-019-1451-2.

Kipnis et al., "T Cell Immunity To Copolymer 1 Confers Neuroprotection On The Damaged 5 Optic Nerve: Possible Therapy For Optic Neuropathies", Proc Natl Acad Sci 2000; 97:7446-7451.

Mysona, Barbara, et al. 2017. "The Role of Sigma 1 Receptor as a Neuroprotective Target in Glaucoma." *Advances in Experimental Medicine and Biology*. https://doi.org/10.1007/978-3-319-50174-1_20.

Ryskamp, Daniel A., Lili Wu, Jun Wu, Dabin Kim, Gerhard Rammes, Michal Geva, Michael Hayden, and Ilya Bezprozvanny. 2019. "Pridopidine Stabilizes Mushroom Spines in Mouse Models of Alzheimer's Disease by Acting on the Sigma-1 Receptor." *Neurobiology of Disease*. https://doi.org/10.1016/j.nbd.2018.12.022.

U.S. Pat. No. 6,903,120, issued Jun. 7, 2005 (Sonesson, et al.)

U.S. Pat. No. 7,923,459, issued Apr. 12, 2011 (Gauthier, et al.)

PCT International Application Publication No. WO 2017/015609

Weinreb et al., "Is Neuroprotection a Viable Therapy for Glaucoma?" Arch Ophthalmol 1999; 117:1540-1544.

What is claimed is:

1. A method of treating, reducing or inhibiting a symptom of a neurodegenerative eye disease in a subject afflicted with a neurodegenerative eye disease comprising administering to the subject a composition pridopidine or pharmaceutically acceptable salt thereof.

2. The method of claim 1, wherein the composition is administered orally or topically.

3. The method of claim 1, wherein the composition is administered intraocularly, intravitreally, periocularly or ocularly.

4. The method of claim 1, wherein the composition is administered by an eye drop application to the conjunctiva.

5. The method of claim 1, wherein the composition is administered in a daily dose, comprising an amount of pridopidine between 22.5 mg/day-315 mg/day.

6. The method of claim 1, wherein the symptom is an optic nerve axon damage or loss or a retinal ganglion cell (RGC) loss or death.

7. The method of claim 6, wherein the composition is effective to reduce or prevent optic nerve axon loss or damage or reduce or prevent a retinal ganglion cell (RGC) loss or death in the subject.

8. The method of claim 7, wherein the optic nerve axon loss is reduced by at least 3%, by at least 5%, by at least 10%, by at least 20%, by at least 30%, by at least 40%, or by at least 50%.

9. The method of claim 7, wherein the optic nerve axon loss is reduced by more than 50%, more than 60%, more than 70%, or more than 80%.

10. The method of claim 1, wherein the composition is effective to protect an optic nerve axon from degeneration in the subject.

11. The method of claim 10, wherein the axon degeneration is induced by elevated intraocular pressure.

* * * * *